United States Patent
Reubinoff

(10) Patent No.: US 8,597,947 B2
(45) Date of Patent: Dec. 3, 2013

(54) UNDIFFERENTIATED STEM CELL CULTURE SYSTEMS

(75) Inventor: Benjamin Reubinoff, Doar Na Haela (IL)

(73) Assignee: Hadasit Medical Research Services & Development Limited, Jerusalem (IL)

( * ) Notice: Subject to any disclaimer, the term of this patent is extended or adjusted under 35 U.S.C. 154(b) by 366 days.

(21) Appl. No.: 11/730,560

(22) Filed: Apr. 2, 2007

(65) Prior Publication Data
US 2007/0212777 A1    Sep. 13, 2007

Related U.S. Application Data

(63) Continuation-in-part of application No. PCT/IL2005/001397, filed on Dec. 29, 2005.

(60) Provisional application No. 60/639,809, filed on Dec. 29, 2004.

(51) Int. Cl.
*C12N 5/00* (2006.01)
*C12N 5/02* (2006.01)
*C12N 5/071* (2010.01)

(52) U.S. Cl.
USPC ........... 435/384; 435/405; 435/383; 435/404; 435/375; 435/366

(58) Field of Classification Search
None
See application file for complete search history.

(56) References Cited

U.S. PATENT DOCUMENTS

| | | | |
|---|---|---|---|
| 5,843,780 A | 12/1998 | Thomson | |
| 5,942,435 A * | 8/1999 | Wheeler | 435/325 |
| 6,180,404 B1 | 1/2001 | Brewer et al. | |
| 6,380,218 B1 | 4/2002 | Marfat et al. | |
| 2003/0143736 A1 | 7/2003 | Bongso et al. | |
| 2003/0161818 A1 | 8/2003 | Weiss et al. | |
| 2004/0136967 A1 | 7/2004 | Weiss et al. | |
| 2005/0037492 A1 | 2/2005 | Xu et al. | |
| 2005/0196864 A1 | 9/2005 | Goldman et al. | |
| 2006/0073591 A1 | 4/2006 | Abitorabi et al. | |
| 2006/0078543 A1 | 4/2006 | Reubinoff et al. | |
| 2006/0211109 A1 | 9/2006 | Totey et al. | |
| 2011/0027333 A1 | 2/2011 | Idelson et al. | |

FOREIGN PATENT DOCUMENTS

| | | |
|---|---|---|
| GB | 2 327 675 A | 2/1999 |
| GB | 2 409 208 A | 6/2005 |
| WO | 98/30679 A1 | 7/1998 |
| WO | 01/55114 A1 | 8/2001 |
| WO | 02/060875 A1 | 8/2002 |
| WO | 03/068233 A1 | 8/2003 |
| WO | 03/078611 A1 | 9/2003 |
| WO | 03/104444 A1 | 12/2003 |
| WO | 2004/031343 A2 | 4/2004 |
| WO | 2004/044158 A2 | 5/2004 |
| WO | 2005/014549 A1 | 2/2005 |
| WO | 2005/086845 A2 | 9/2005 |
| WO | 2006/070370 A2 | 7/2006 |
| WO | 2007/002086 A2 | 1/2007 |

OTHER PUBLICATIONS

Gerami-Naini,B et al, 2004, Trophoblast differentiation in embryoid vodies derived from human embyonic stem cells, Endocrinology, 145:1517-1524.*
Vallier, Journal of Cell Science, 2005. 118:4495-4509.*
Amit et al., Biol. of Reprod., 70: 837-845, 2004.*
Humphrey et al. (2004) Stem Cells 22: 522-530.*
Xu et al. (2005) Nature Methods 2:185-190.*
Thomson et al. PNAS, 92:7844-7848 Aug. 1995.*
Valdimarsdottir et al., Functions of the TGFb superfamily in human embryonic stem cells. APMIS, 113(11-12):773-89, 2005.*
Brewer et al., "Optimized Survival of Hippocampal Neurons in B27-Supplemented Neurobasal™, a New Serum-Free Medium Combination" J Neurosci Res 35:567-576 (1993).
Reubinoff, et al., "Embryonic stem cell lines from human blastocysts: somatic differentiation in vitro", Nature Biotechnology, (2000), vol. 18, pp. 399-404.
Amit, et al., "Clonally Derived Human Embryonic Stem Cell Lines Maintain Pluripotency and Proliferative Potential for Prolonged Periods of Culture", Developmental Biology, (2000), vol. 227, pp. 271-278.
Xu, et al., "Feeder-free growth of undifferentiated human embryonic stem cells", Nature Biotechnology, (2001), vol. 19, pp. 971-974.
Cowan, et al., "Derivation of Embryonic Stem-Cell Lines from Human Blastocysts", The New England Journal of Medicine, (2004), vol. 350, No. 13, pp. 1353-1356.
Pera, et al., "Regulation of human embryonic stem cell differentiation by BMP-2 and its antagonist noggin", Journal of Cell Science, (2004), vol. 117, pp. 1269-1280.
Xu, et al., "Basic FGF and suppression of BMP signaling sustain undifferentiated proliferation of human ES cells", Nature Methods, (2005), vol. 2, No. 3, pp. 185-190.
Itsykson, et al., "Derivation of neural precursors from human embryonic stem cells in the presence of noggin", Mol. Cell. Neurosci., (2005), vol. 30, pp. 24-36.
Yan, et al., "Directed Differentiation of Dopaminergic Neuronal Subtypes from Human Embryonic Stem Cells", Stem Cells, (2005), vol. 23, pp. 781-790.
Ludwig, et al., "Derivation of human embryonic stem cells in defined conditions", Nature Biotechnology, (2006), vol. 24, No. 2, pp. 185-87.

(Continued)

*Primary Examiner* — Valarie Bertoglio
(74) *Attorney, Agent, or Firm* — Vorys, Sater, Seymour and Pease LLP; Susanne M. Hopkins; Ari G. Zytcer

(57) ABSTRACT

The present application discloses methods expanding SCs in an undifferentiated state, the methods comprising incubating undifferentiated SCs in suspension within a culture system comprising basic medium and knockout serum replacement (KOSR). The methods may also be applicable for selective spontaneous or directed differentiation of SCs into a selected population of somatic cells from a culture system of SCs in suspension, the method further comprising incubating said undifferentiated SCs in culture system that support respectively, spontaneous or directed differentiation of SCs into the selected population of somatic cells. The present application also discloses a culture system for expansion of stem cells (SCs) comprising a suspension of undifferentiated stem cells within basic medium and knockout serum replacement (KOSR). The methods and culture system of the invention may be used for large scale production of differentiated cells.

20 Claims, 13 Drawing Sheets

(56) References Cited

OTHER PUBLICATIONS

Kallos, et al., "Large-scale expansion of mammalian neural stem cells: A review", Med. Biol. Eng. Comput., (2003), vol. 41, pp. 271-282.

Gerecht-Nir, et al., "Bioreactor Cultivation Enhances the Efficiency of Human Embryoid Body (hEB) Formation and Differentiation", Biotechnology and Bioengineering, (2004), vol. 86, No. 5, pp. 493-502.

Goldsborough, et al., "Serum-free culture of murine embryonic stem (ES) cells", Focus, (1998), vol. 20, No. 1, pp. 8-12.

Reubinoff, et al., "Identification and Maintenance of Neural Precursors from Human Embryonic Stem Cells", Handbook of Stem Cells, (2004), vol. 1, Chapter 49, pp. 511-520.

Klimanskaya, et al., "Human embryonic stem cell lines derived from single blastomeres", Nature, (2006), vol. 444, pp. 481-485, ADDENBUM.

D'Amour, et al., "Production of pancreatic hormone-expressing endocrine cells from human embryonic stem cells", Nature Biotechnology, (2006), vol. 24, No. 11, pp. 1392-1401.

Yao, et al., "Long-term self-renewal and directed differentiation of human embryonic stem cells in chemically defined conditions", PNAS, (2006), vol. 103, No. 18, pp. 6907-6912.

Turetsky, et al., "Laser-assisted derivation of human embryonic stem cell lines from IVF embryos after preimplantation genetic diagnosis", Human Reproduction, (2008), vol. 23, No. 1, pp. 46-53.

Thomson, et al., "Private Embryonic Stem Cells", Current Topics in Developmental Biology, (1998), vol. 38, Chapter 4, pp. 133-165.

Thomson, et al., "Isolation of a primate embryonic stem cell line", Proc. Natl. Acad. Sci. USA, (1995), vol. 92, pp. 7844-7848.

Bongso, et al., "Improved quality of human embryos when co-cultured with human ampullary cells", Human Reproduction, (1989), vol. 4, No. 6, pp. 706-713.

Gardner, et al., "Culture and transfer of human blastocysts increases implantation rates and reduces the need for multiple embryo transfers", Fertility and Sterility, (1998), vol. 69, No. 1, pp. 84-88.

Thomson, et al., "Embryonic Stem Cell Lines Derived from Human Blastocysts", Science, (1998), vol. 282, pp. 1145-1147.

Carpenter, et al., "Characterization and Differentiation of Human Embryonic Stem Cells", Cloning and Stem Cells, (2003), vol. 5, No. 1, pp. 79-88.

Brewer, "Serum-free B27/Neurobasal medium supports differential growth of neurons from the striatum, substantia nigra, septum, cerebral cortex, cerebellum, and dentate gyrus", Journal of Neuroscience Research, (1995), vol. 42, pp. 674-683.

Gearhart, "New Potential for Human Embryonic Stem Cells", Science, (1998), vol. 282, No. 5391, pp. 1061-1062.

Rossant, et al., "In search of the tabula rasa of human cells", Nature Biotechnology, (1999), vol. 17, pp. 23-24.

Martin, et al., "Human embryonic stem cells express an immunogenic nonhuman sialic acid", Nature Medicine, (2005), vol. 11, No. 2, pp. 228-232.

Richards, et al., "Human feeders support prolonged undifferentiated growth of human inner cell masses and embryonic stem cells", Nature Biotechnology, (2002), vol. 20, pp. 933-936.

Vaca, et al., "Nicotinamide Induces Both Proliferation and Differentiation of Embryonic Stem Cells Into Insulin-Producing Cells", Transplantation Proceedings, (2003), vol. 35, pp. 2021-2023.

Haruta, et al., "In vitro and in vivo characterization of pigment epithelial cells differentiated from primate embryonic stem cells", Invest Ophthalmol Vis Sci, (2004), vol. 45, pp. 1020-1025.

Ohno-Matsui, et al., "In vitro and in vivo characterization of iris pigment epithelial cells cultured on amniotic membranes", Molecular Vision, (2006), vol. 12, pp. 1022-1032.

Conti, et al., "Niche-independent symmetrical self-renewal of a mammalian tissue stem cell", PLoS Biology, (2005), vol. 3, Issue 9, pp. 1594-1606.

Coucouvanis, et al., "Signals for death and survival: a two-step mechanism for cavitation in the vertebrate embryo", Cell, (1995), vol. 83, pp. 279-287.

Doetschman, et al., "The in vitro development of blastocyst-derived embryonic stem cell lines: formation of visceral yolk sac, blood islands and myocardium", J. Embryol. exp. Morph., vol. 87, pp. 27-45, (1985).

Roach, et al., "Hepatocytic transcription factor expression in human embryonal carcinoma and yolk sac carcinoma cell lines: expression of HNF-3α in models of early endodermal cell differentiation", Experimental Cell Research, (1994), vol. 215, pp. 189-198.

Kemler, et al., "Reactivity of monoclonal antibodies against intermediate filament proteins during embryonic development", J. Embryol. exp. Morph., (1981), vol. 64, pp. 45-60.

Smith, et al., "Risk Factors for Age-related Macular degeneration: Pooled findings from three continents", Ophthalmology, (2001), vol. 108, pp. 697-704.

Nakayama, et al., "A novel chordin-like protein inhibitor for bone morphogenetic proteins expressed preferentially in mesenchymal cell lineages", Developmental Biology, (2001), vol. 232, pp. 372-387.

Abreu, et al., "Chordin-like CR domains and the regulation of evolutionarily conserved extracellular signaling systems", Gene, (2002), vol. 287, pp. 39-47.

Troyer, et al., "Concise Review: Wharton's Jelly-Derived Cells Are a Primitive Stromal Cell Population", Stem Cells, (2008), vol. 26, pp. 591-599.

Richards, et al., "Comparative Evaluation of Various Human Feeders for Prolonged Undifferentiated Growth of Human Embryonic Stem Cells", Stem Cells, (2003), vol. 21, pp. 546-556.

Zhang, et al., "The comparison of biologic character between mouse embryonic fibroblast and human embryonic fibroblast", (2003), My NCBI, vol. 20, No. 2, pp. 251-254 (abstract only).

Draper, et al., "Culture and Characterization of Human Embryonic Stem Cells", Stem Cells and Development, (2004), vol. 13, pp. 325-336.

Amit, et al., "Human Feeder Layers for Human Embryonic Stem Cells", Biology of Reproduction, (2003), vol. 68, pp. 2150-2156.

Bodnar, et al., "Propagation and Maintenance of Undifferentiated Human Embryonic Stem Cells", Stem Cells and Development, (2004), vol. 13, pp. 243-253.

Kohler, et al., "Defining Optimum Conditions for the Ex Vivo Expansion of Human Umbilical Cord Blood Cells. Influences of Progenitor Enrichment, Interference with Feeder Layers, Early-Acting Cytokines and Agitation of Culture Vessels", Stem Cells, (1999), vol. 17, pp. 19-24.

Amit, et al., "Feeder Layer- and Serum-Free Culture of Human Embryonic Stem Cells", Biology of Reproduction, (2004), vol. 70, pp. 837-845.

Cameron, et al., "Improved Development of Human Embryonic Stem Cell-Derived Embryoid Bodies by Stirred Vessel Cultivation", Biotechnology and Bioengineering, (2006), vol. 94, No. 5, pp. 938-948.

Cormier, et al., "Expansion of Undifferentiated Murine Embryonic Stem Cells as Aggregates in Suspension Culture Bioreactors", Tissue Engineering, (2006), vol. 12, No. 11, pp. 3233-3245.

Ye, et al., "Establishment of an adherent cell feeder layer from human umbilical cord blood for support of long-term hematopoietic progenitor cell growth", Proc. Natl. Acad. Sci. USA, vol. 91, pp. 12140-12144, (1994).

Dang, et al., "Efficiency of Embryoid Body Formation and Hematopoietic Development from Embryonic Stem Cells in Different Culture Systems", Biotechnology and Bioengineering, (2002), vol. 78, No. 4, pp. 442-453.

Fok, et al., "Shear-Controlled Single-Step Mouse Embryonic Stem Cell Expansion and Embryoid Body-Based Differentiation", Stem Cells, (2005), vol. 23, pp. 1333-1342.

Gerami-Naini, et al., "Trophoblast Differentiation in Embryoid Bodies Derived from Human Embryonic Stem Cells", Endocrinology, (2004), vol. 145, No. 4, pp. 1517-1524.

Nieden, et al., "Embryonic stem cells remain highly pluripotent following long term expansion as aggregates in suspension bioreactors", Journal of Biotechnology, (2007), vol. 129, pp. 421-432.

Steiner, et al., "Derivation, propagation and controlled differentiation of human embryonic stem cells in suspension", Nature Biotechnology, (2010), vol. 28, No. 4, pp. 361-366.

(56) References Cited

OTHER PUBLICATIONS

Ulloa-Montoya, et al., "Culture Systems for Pluripotent Stem Cells", Journal of Bioscience and Bioengineering, (2005), vol. 100, No. 1, pp. 12-27.

Vallier, et al., "Activin/Nodal and FGF pathways cooperate to maintain pluripotency of human embryonic stem cells", Journal of Cell Science, (2005), vol. 118, No. 19, pp. 4495-4509.

Van Dijk, et al., "Kinetics and regulation of site-specific endonucleolytic cleavage of human IGF-II mRNAs", Nucleic Acids Research, vol. 29, No. 17, pp. 3477-3486, (2001).

Brewer, et al., "Optimized Survival of Hippocampal Neurons in B27-Supplemented Neurobasal, a New Serum-free Medium Combination", Journal of Neuroscience Research, vol. 35, pp. 567-576, (1993).

Amit, et al., "Human Embryonic Stem Cells: Laboratory Manual", pp. 1-42, (2002), (c) Technion—Israeli Institute of Technology.

Aoki, et al. "Embryonic stem cells that differentiate into RPE cell precursors in vitro develop into RPE cell monolayers in vivo", Experimental Eye Research, vol. 82, pp. 265-274, (2006).

Chang, et al., "Blastocyst formation, karyotype, and mitochondrial DNA of interspecies embryos derived from nuclear transfer of human cord fibroblasts into enucleated bovine oocytes", Fertility and Sterility, vol. 80, No. 6, pp. 1380-1387, (2003).

Fryer, et al., "Human Endothelium in Cell Culture", J. Atheroscler. Res.", vol. 6, pp. 151-163, (1966).

Houtenbos, et al., "Serum-free generation of antigen presenting cells from acute myeloid leukaemic blasts for active specific immunisation", Cancer Immunol. Immunother, vol. 52, pp. 455-462, (2003).

Idelson, et al., "Directed Differentiation of Human Embryonic Stem Cells into Functional Retinal Pigment Epithelium Cells", Cell Stem Cell, vol. 5, pp. 396-408, (2009).

Kawasaki, et al., "Generation of dopaminergic neurons and pigmented epithelia from primate ES cells by stromal cell-derived inducing activity", PNAS, vol. 99, No. 3, pp. 1580-1585, (2002).

Lam, et al., "Preclinical ex vivo expansion of cord blood hematopoietic stem and progenitor cells: duration of culture; the media, serum supplements, and growth factors used; and engraftment in NOD/SCID mice", Transfusion, vol. 41, pp. 1567-1576, (2001).

Laslett, et al., "Characterization and Culture of Human Embryonic Stem Cells", TCM, vol. 13, No. 7, pp. 295-301, (2003).

Moog, et al., "Platelet glycoprotein V binds to collagen and participates in platelet adhesion and aggregation", Blood, vol. 98, pp. 1038-1046, (2001).

Nakamura, et al., "Morphologic evaluation of the antitumor activity of photodynamic therapy (PDT) using mono-L-aspartyl chlorin e6 (NPe6) against uterine cervical carcinoma cell lines", Int J Gynecol Cancer, vol. 12, pp. 177-186, (2002).

Rao, et al., "Culture development for human embryonic stem cell propagation: molecular aspects and challenges", Current Opinion in Biotechnology, vol. 16, pp. 568-576, (2005).

Reubinoff, et al., "Neural progenitors from human embryonic stem cells", Nature Biotechnology, vol. 19, pp. 1134-1140, (2001).

Shen, et al., "Protective Effect of Nicotinamide on Neuronal Cells under Oxygen and Glucose Deprivation and Hypoxia/Reoxygenation", J Biomed Sci, vol. 11, pp. 472-481, (2004).

Suemori, et al., "Establishment of Embryonic Stem Cell Lines From Cynomolgus Monkey Blastocysts Produced by IVF or ICSI", Developmental Dynamics, vol. 222, pp. 273-279, (2001).

Thoennes, et al., "Differential transcriptional activation of peroxisome proliferator-activated receptor gamma by omega-3 and omega-6 fatty acids in MCF-7 cells", Molecular and Cellular Endocrinology, vol. 160, pp. 67-73, (2000).

\* cited by examiner

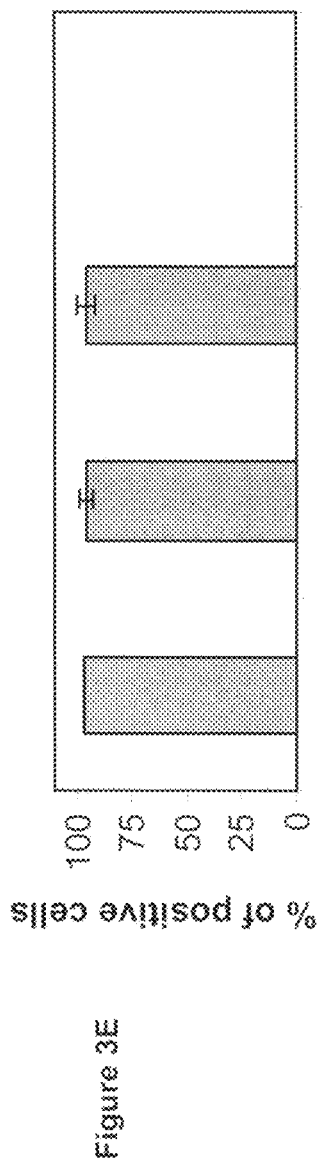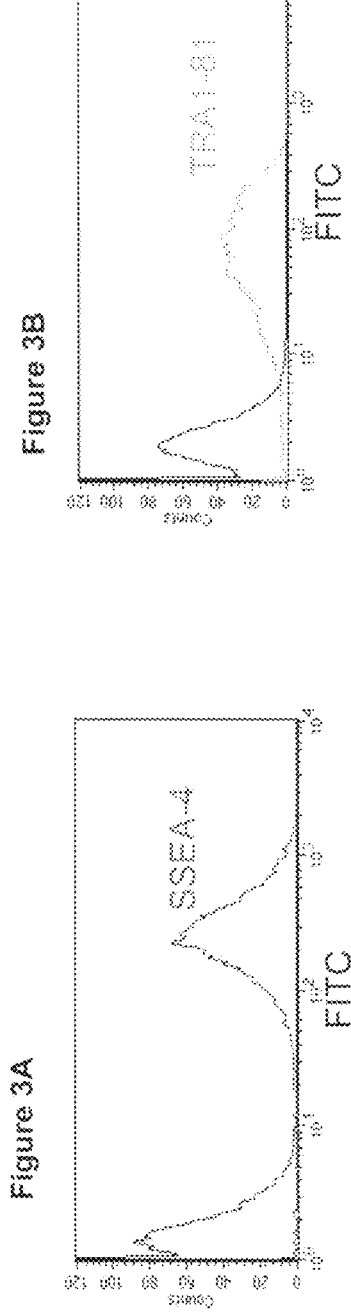
Figure 3A, Figure 3B, Figure 3C, Figure 3D, Figure 3E

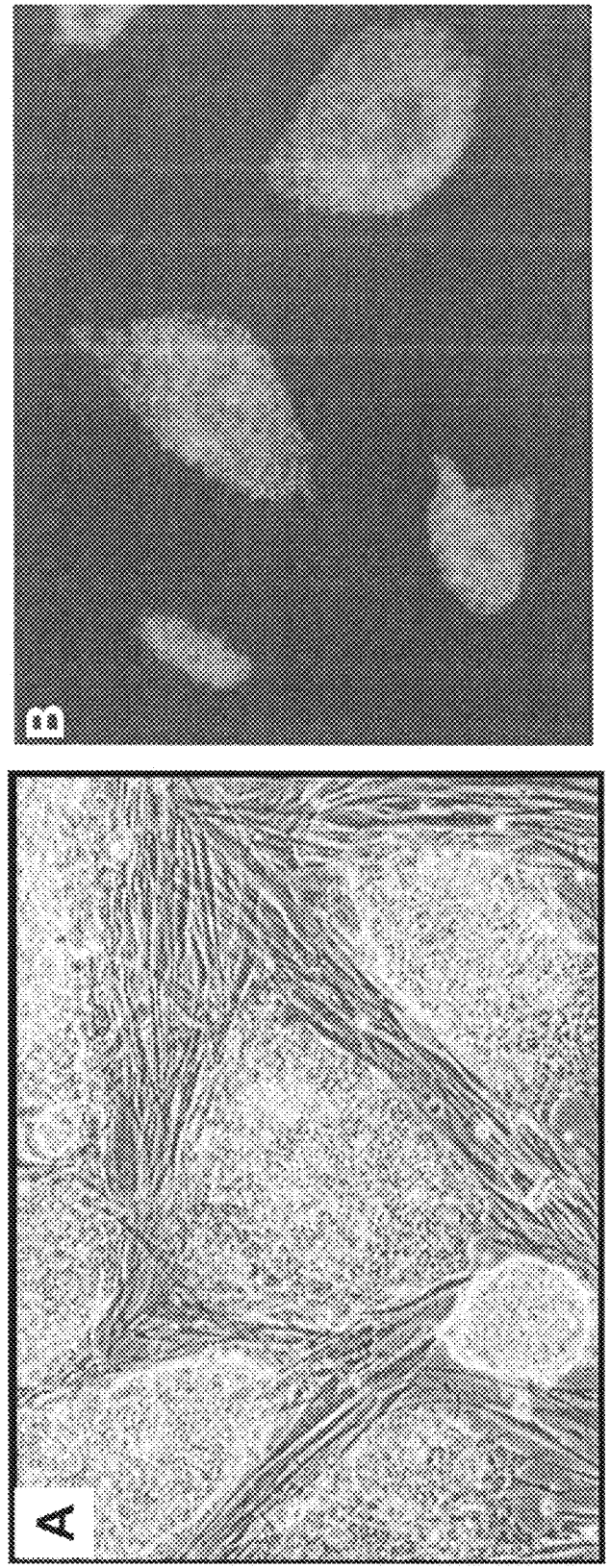

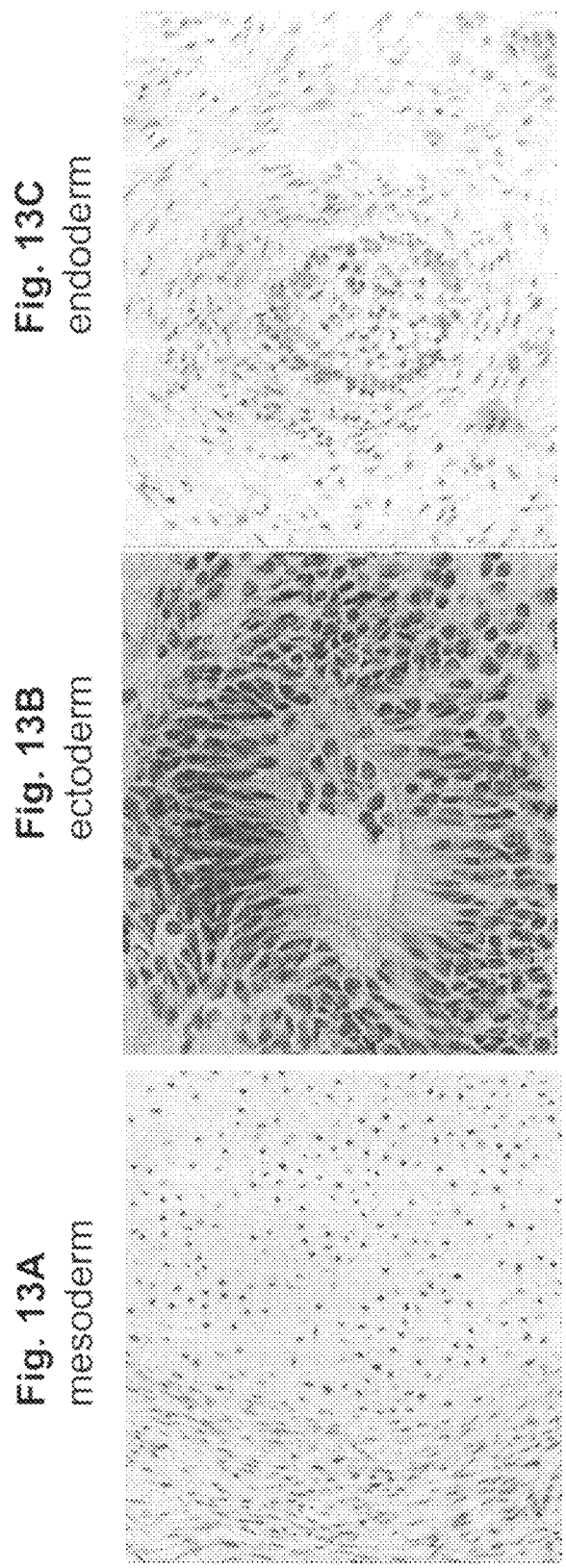

UNDIFFERENTIATED STEM CELL CULTURE SYSTEMS

RELATED APPLICATION

This application is a Continuation-in-Part application of PCT/IL2005/001397 (published as WO06/07037), which derives priority from U.S. Provisional Application No. 60/639,809. This application hereby incorporates by reference the entire contents of WO06/07037.

FIELD OF THE INVENTION

This invention relates to stem cells (SC), and particularly to methods and systems for handling and propagating human embryonic stem cells (hESC).

LIST OF RELATED ART

The following is a list of references which are considered to be pertinent for describing the state of the art in the field of the invention.

(1) Reubinoff, B. E., Pera, M. F., Fong, C. Y., Trounson, A. & Bongso, A. Embryonic stem cell lines from human blastocysts: somatic differentiation in vitro. *Nat Biotechnol* 18, 399-404 (2000)
(2) Amit, M. et al. Clonally derived human embryonic stem cell lines maintain pluripotency and proliferative potential for prolonged periods of culture. *Dev Biol* 227, 271-278 (2000).
(3) Xu, C. et al. Feeder-free growth of undifferentiated human embryonic stem cells. *Nat Biotechnol* 19, 971-974 (2001).
(4) Amit, M. et al. Human feeder layers for human embryonic stem cells. *Biol Reprod* 68, 2150-2156 (2003).
(5) Richards, M., Fong, C. Y., Chan, W. K., Wong, P. C. & Bongso, A. Human feeders support prolonged undifferentiated growth of human inner cell masses and embryonic stem cells. *Nat Biotechnol* 20, 933-936 (2002).
(6) Cowan, C. A. et al. Derivation of embryonic stem-cell lines from human blastocysts. *N Engl J Med* 350, 1353-1356 (2004).
(7) Amit, M., Shariki, C., Margulets, V. & Itskovitz-Eldor, J. Feeder layer- and serum-free culture of human embryonic stem cells. *Biol Reprod* 70(3):837-45 (2004).
(8) Pera, M. F. et al. Regulation of human embryonic stem cell differentiation by BMP-2 and its antagonist noggin. *J Cell Sci* 117, 1269-1280 (2004).
(9) GB 2409208.
(10) WO04/031343.
(11) Xu, R. H., et al. Basic FGF and suppression of BMP signaling sustain undifferentiated proliferation of human ES cells. *Nat Methods.* 3, 164-5 (2005).
(12) Vallier L, et al. Activin/Nodal and FGF pathways cooperate to maintain pluripotency of human embryonic stem cells. *J Cell Sci.* 118, 4495-509 (2005).
(13) WO 06/070370 (Reubinoff, B. et al.).
(14) Itsykson, P., et al. Derivation of neural precursors from human embryonic stem cells in the presence of noggin. *Mol Cell Neurosci* 30(1), 24-36 (2005).
(15) Yan, Y. et al. Directed differentiation of dopaminergic neuronal subtypes from human embryonic stem cells. *Stem Cells* 23(6), 781-90 (2005).
(16) Ludwig, T. E. et al. Derivation of human embryonic stem cells in defined conditions. *Nat Biotechnol* 24(2), 185-87 (2006).
(17) Kallos, M. S. et al. Large-scale expansion of mammalian neural stem cells: A review. *Med Biol Eng Comput* 41(3), 271-82 (2003).
(18) Cormier, J. T., et al. Expansion of Undifferentiated Murine Embryonic Stem Cells as Aggregates in Suspension Culture Bioreactors. *Tissue Eng* 1, 1 (2006).
(19) Fok, E. Y. et al. Shear-controlled single-step mouse embryonic stem cell expansion and embryoid body-based differentiation. *Stem Cells* 23(9), 1333-42 (2005).
(20) Gerecht-Nir, S. et al. Bioreactor cultivation enhances the efficiency of human embryoid body (hEB) formation and differentiation. *Biotechnol Bioeng* 86(5), 493-502 (2004).
(21) Goldsborough, M. D. et al. Serum-free culture of murine embryonic stem (ES) cells. *Focus* 20(1), 8-12 (1998).
(22) WO 98/30679.
(23) WO 03/104444.
(24) Reubinoff B E, Khaner H. Identification and Maintenance of Neural Progenitors from human ES cells. In Handbook Of Stem Cells, Volume 2: Embryonic Stem Cells. Lanza R, Gearhart J D, Hogan B L M, Mckay R D, Melton D A, Pedersen R, Thomson J A West M D (eds). Academic Press 2004, pages 511-520.
(25) Klimanskaya I, Chung Y, Becker S, Lu S J, Lanza R. Human embryonic stem cell lines derived from single blastomeres. Nature. Mar. 15, 2007; 446(7133):342.
(26) D'Amour K A, Bang A G, Eliazer S, Kelly O G, Agulnick A D, Smart N G, Moorman M A, Kroon E, Carpenter M K, Baetge E E. Production of pancreatic hormone-expressing endocrine cells from human embryonic stem cells. Nat Biotechnol. November 2006; 24(11):1392-401.
(27) Yao S, Chen S, Clark J, Hao E. Beattie G M Hayek A and Ding S. Long-term self-renewal and directed differentiation of human embryonic stem cells in chemically defined conditions. PNAS 2006; 103: 6907-6912.

BACKGROUND OF THE INVENTION

Stem cells are immature, unspecialized cells that renew themselves for long periods through cell division. Under certain conditions, they can differentiate into mature, functional cells. Human embryonic stem cells (hESC) are derived from early surplus human blastocysts[1]. Human ES cells are unique stem cells since they can self-renew infinitely in culture, and since they have a remarkable potential to develop into extraembryonic lineages as well as all somatic cells and tissues of the human body[1].

Given the unique properties of hESC, they are expected to have far-reaching applications in the areas of basic scientific research, pharmacology, and regenerative medicine. Human ES cell lines can provide a powerful in vitro model for the study of the molecular and cellular biology of early human development, for functional genomics, drug screening, and discovery. They may serve for toxicology and teratogenicity high throughput screening. Since hESC can self-renew indefinitely and can differentiate into any cell type, they can serve as a renewable, unlimited donor source of functionally mature differentiated cells or tissues for transplantation therapy. In addition, transplanted genetically-modified hESC can serve as vectors to carry and express genes in target organs in the course of gene therapy.

While the promise of hESC for basic scientific research pharmacology and regenerative medicine is remarkable, the exploitation of hESC for most applications depends upon further development. Improved control of the growth of undifferentiated hESC, the development of bulk feeder-free cultures of undifferentiated cells, the development of animal-free culture systems, and the development of methods and tools which direct the differentiation and generate pure cultures of mature functional cells of a specific type are required.

At present, a few culture systems are most commonly used to propagate undifferentiated hESC[1-3]. In the initial culture system that was developed, undifferentiated hESC are cultured in serum-containing medium as colonies, upon a layer of fibroblast feeder cells (of mouse[1] or human origin[4, 10]). It is possible to remove all animal products from this culture system and replace them with those from a human source[5]. It was found that in this system the cells are propagated as clumps on a small scale, which does not allow cloning[2].

An alternative culture system for use in the proliferation of undifferentiated growth of hESC comprises a culture matrix comprising extracellular matrix (ECM) that may be prepared from feeder cells or other sources and a conditioned medium being preconditioned by feeder cells. The suggested leading cells in the feeder cells include primary mouse embryonic fibroblasts (PMEF), a mouse embryonic fibroblast cell line (MEF), murine foetal fibroblasts (MFF), human embryonic fibroblasts (HEF), human foetal muscle (HFM), human foetal skin cells (HFS), human adult skin cells, human foreskin fibroblasts (HFF)[9], human adult Fallopian tubal epithelial cells (HAFT), or human marrow stromal cells (HMSC).

Another alternative culture system that was developed and used extensively is a serum-free system that includes the knockout (KO) medium supplemented with knockout serum replacement (KOSR) and FGF2. This system allows cloning of undifferentiated hESC, although at a low efficiency[2]. Undifferentiated cells are cultured as flat colonies and may be propagated mechanically as small clusters or single cells (by using trypsin[6]).

Knockout serum replacement (KOSR) (Gibco) is a chemically defined, serum-free culture medium supplement used as a substitute for animal-based serum in KO-DMEM-based culture systems for propagating stem cells. KOSR can efficiently promote the growth and maintenance of undifferentiated embryonic stem cells and therefore may replace the supplementation with fetal bovine serum (FBS)[21], KO-DMEM may replace traditional DMEM in either FBS- or KOSR-supplemented cultures[21].

Undifferentiated propagation of adherent colonies of hESCs may be accomplished with a KO serum-free culture system without the use of feeders by plating and growing the colonies on extracellular matrices (ECM) within a feeder-conditioned KO-DMEM medium supplemented with KOSR and FGF2[3]. Furthermore, it has been suggested that feeder conditioning may be replaced by substituting the medium with high concentrations of FGF2 and noggin[11]. Alternatively, feeder conditioning was replaced by transforming growth factor ⊕1 and human LIF (in addition to FGF2) and growing the cells on human fibronectin[7], or by serum-free media supplemented with soluble factors including FGF2, activin A, transforming growth factor β1 (TGFβ1), pipecolic acid, GABA, LiCL and culturing the cells on ECM components(16). In another recent publication, undifferentiated propagation of hESC colonies, in the absence of feeders, was reported with a chemically defined medium without serum replacer, supplemented with activin or nodal plus FGF2[12]. In general, a key limitation of hESC culture systems is that they do not allow the propagation of pure populations of undifferentiated stem cells and their use typically involves some level of background differentiation. The stem cells most commonly follow a default pathway of differentiation into an epithelial cell type that grows either as a monolayer of flat squamous cells or form cystic structures. Most probably, this form of differentiation represents differentiation of hESC into extraembryonic endoderm[8].

In these adherent culture systems of colonies, the hESCs are most commonly propagated (mechanically and/or by using enzymatic digestion) as clusters, on a small scale. These culture systems are labor-intensive, highly variable, may contain undefined factors, and do not provide steady-state operating conditions. Most importantly, they do not typically allow for large scale production of standardized homogenous undifferentiated hESCs needed for the aforementioned uses.

Suspension culture bioreactors offer several advantages over the conventional use of static monolayer cultures. These systems facilitate the large-scale expansion of the cells in a homogeneous culture environment, thus decreasing the risk of culture variability. They are also less labor-intensive to operate and offer the possibility of computer control and monitoring of the culture conditions. Although bioreactors have been used to expand neural stem cells[17], mouse ES cells[18] and differentiating hESCs within embryoid bodies (EBs)(20), only recently some progress has been made towards the development of protocols for the feeder-free expansion of undifferentiated hESCs in suspension systems[13].

A major obstacle in developing systems for culturing hESCs in suspension bioreactors was recently overcome when it was demonstrated that hESCs may be propagated, in the pluripotent, undifferentiated state, as clusters in suspension, using Neurobasal™ medium as the basic medium of the culture system[13], which is supplemented with N2. Neurobasal™ medium is a basal medium especially formulated for growth of neuronal cells, and supplemented with either serum (e.g., FBS) or B27 or N2 serum replacement[23].

The following is the composition of Neurobasal™ medium:

| Component | Concentration in μM |
|---|---|
| inorganic salts | |
| $CaCl_2$ (anhydrous) | 1800 |
| $Fe(NO_3)_3\ 9H_2O$ | 0.2 |
| KCl | 5360 |
| $MgCl_2$ (anhydrous) | 812 |
| NaCl | 76000 |
| $NaHCO_3$ | 880 |
| $NaH_2PO_4\ H_2O$ | 900 |
| $ZnSO_4\ 7H_2O$ | 0.67 |
| other components | |
| D-glucose | 25000 |
| phenol red | 23 |
| MOPS | 10000 |
| sodium pyruvate | 230 |
| amino acids | |
| L-alanine | 20 |
| L-arginine HCl | 400 |
| L-asparagine $H_2O$ | 5 |
| L-cysteine | 10 |
| L-glutamine | 500 |
| glycine | 400 |
| L-histidine HCl $H_2O$ | 200 |
| L-isoleucine | 800 |
| L-leucine | 800 |
| L-lysine HCl | 5 |
| L-methionine | 200 |
| L-phenylalanine | 400 |
| L-proline | 67 |
| L-serine | 400 |
| L-threonine | 800 |
| L-tryptophan | 80 |
| L-tyrosine | 400 |
| L-valine | 800 |

-continued

| Component | Concentration in µM |
|---|---|
| vitamins | |
| D-Ca pantothenate | 8 |
| choline chloride | 28 |
| folic acid | 8 |
| i-inositol | 40 |
| niacinamide | 30 |
| pyridoxal HCl | 20 |
| riboflavin | 1 |
| thiamine HCl | 10 |
| vitamin B12 | 0.2 |

SUMMARY OF THE INVENTION

The present invention is based on the surprising finding that supplementing Neurobasal™ medium with KO serum replacement (KOSR) instead of with N2 significantly increased level of expansion of undifferentiated and pluripotent stem cells cultivated in a suspension. Specifically, the results provided hereinbelow show that after 3 weeks the total number of undifferentiated and pluripotent human embryonic stem cells (hESCs) propagated in NBSR medium reached a population of approximately double that of NBN2-cultured hESCs.

Further, it was surprisingly found that the NBSR medium could effectively support long-term cultivation of undifferentiated pluripotent hESCs. The specific, non-limiting examples provided hereinbelow show that the percentage of hESCs expressing markers of pluripotent stem cells (SSEA4, TRA1-60, and TRA1-81) was high (>95%) and stable after 3.5 weeks and 6.5 weeks of suspension culture.

Furthermore, it was surprisingly found that NBSR medium supplemented with Nutridoma-CS did not require the addition of laminin.

Thus, in accordance with a first of its aspects, the present invention provides a culture system for expansion of stem cells (SCs) comprising a suspension of undifferentiated stem cells within basic medium and knockout serum replacement (KOSR). Preferably, the basic medium is Neurobasal™.

In accordance with a second aspect, the invention provides a method of expanding SCs in an undifferentiated state, the method comprising incubating undifferentiated SCs in suspension in a culture system comprising basic medium and knockout serum replacement (KOSR).

In accordance with a third aspect, the invention provides a method of promoting directed differentiation of SCs to a selected population of somatic cells, the method comprising:
 (a) providing a culture system comprising a suspension of undifferentiated SCs in accordance with the invention;
 (b) incubating said undifferentiated SCs in culture system that support directed differentiation of SCs into the selected somatic cells.

In accordance with one embodiment, the selected population of somatic cells consists essentially of neural precursor cells. In accordance with another embodiment the selected population of somatic cells consists essentially of dopaminergic neuronal cells. Culture systems which support directed differentiation of SC's into a specifically desirable type of somatic cell, such as neural precursor cells or dopaminergic neuronal cells are well known in the art.

In accordance with a fourth aspect, the invention provides a method of promoting spontaneous differentiation of SCs into somatic cells, the method comprising:
 (a) providing a culture system comprising a suspension of undifferentiated SCs in accordance with the invention;
 (b) incubating said undifferentiated SCs in culture system that support spontaneous differentiation of SCs into the somatic cells.

The somatic cells in accordance with this aspect of the invention may comprise cells from the three embryonic germ layers: ectoderm; mesoderm; and endoderm. Thus, the method of the invention for promoting spontaneous differentiation of somatic cells so as to provide a population of somatic cells comprising a single cell type as well as a mixture of ectodermal, mesodermal and/or endodermal cells Culture systems which support spontaneous differentiation of SC's into somatic cells, are well known in the art.

In accordance with a fifth aspect, the invention provides the use of KOSR for the preparation of a culture system for expanding in suspension undifferentiated SCs.

BRIEF DESCRIPTION OF THE DRAWINGS

In order to understand the invention and to show how it may be carried out in practice, a preferred embodiment will now be described, by way of non-limiting example only, with reference to the accompanying drawings, in which:

FIGS. 3A-3E: are FACS analysis images of hESC clusters that were cultured 3 weeks in suspension and dissociated into single cells and showing that >90% of the cells expressed markers of pluripotency SSEA-4 (FIG. 3A), TRA1-60 (FIG. 3B), TRA1-81 (FIG. 3C) and, but not a marker of early neural differentiation, PSA-NCAM (FIG. 3D). Summary of two independent experiments are presented in the bar graph histograms (FIG. 3E);

FIG. 4A-4B are phase contrast image (FIG. 4A) and fluorescence image (FIG. 4B) of colonies of undifferentiated hESCs developed after plating clusters that were cultivated in suspension and then replated on feeders with typical morphology (FIG. 4A), and with cells within the adherent colonies expressing alkaline phosphatase (FIG. 4B).

FIGS. 13A-13C: are images of histological sections of teratoma tumors that developed after inoculation of hESCs, cultivated in suspension for 7 weeks, into the testes of NOD/SCID mice. Differentiated progeny representing the three embryonic germ layers, mesoderm (FIG. 13A), ectoderm (FIG. 13B) and endoderm (FIG. 13C) are illustrated.

DETAILED DESCRIPTION OF EXEMPLARY EMBODIMENTS

Figure 1:
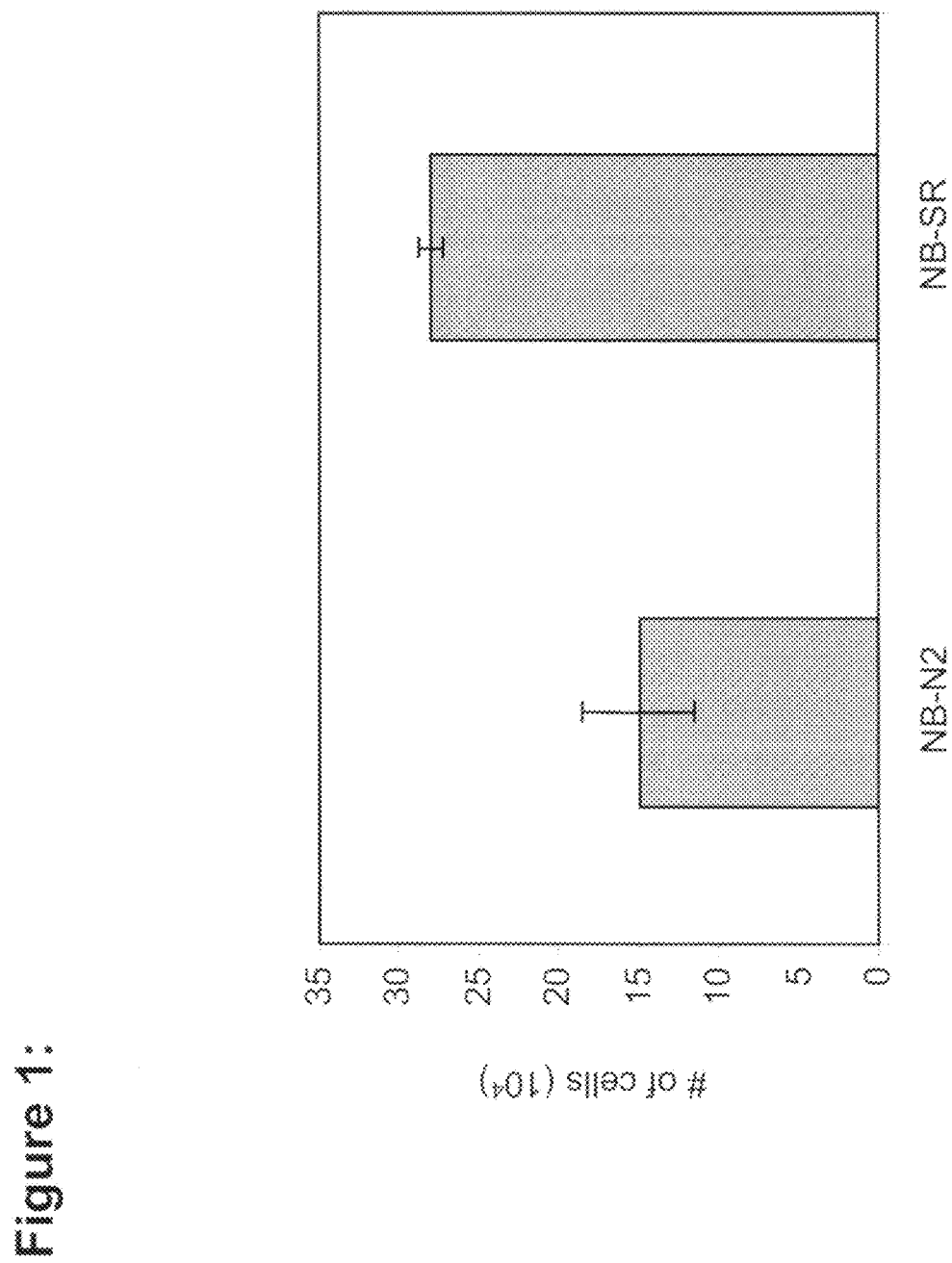
FIG. 1: is a bar graph showing the number of stem cells in a suspension culture system comprising Neurobasal™ (NB) medium as the basic medium supplemented with KOSR (NBSR) or with N2 (NBN2); Cell counts were performed 3 weeks after transfer of equal number of clusters of undifferentiated hESCs into suspension culture within the two media compositions.

The invention is described in the following detailed description with reference to culture systems for handling stem cells, preferably human embryonic stem cells. It should be noted that in addition to the culture systems discussed in detailed hereinbelow, also encompassed within the present invention are uses of specific components described with reference to the culture system in the preparation of such stem cell cultures, as well as to methods of use of the culture system in handling stem cell cultures and methods of preparing cultured cells.

As used in the specification and claims, the forms "a", "an" and "the" include singular as well as plural references unless the context clearly dictates otherwise. For example, the term "a stem cell" includes one or more stem cells, and the term "stem cells" includes one stem cell as well as more than one stem cell.

As used herein, the term "or" means one or a combination of two or more of the listed choices.

Further, as used herein, the term "comprising" is intended to mean that the methods and culture systems includes the recited elements, but does not exclude others. Similarly, "consisting essentially of" is used to define methods and systems that include the recited elements but exclude other elements that may have an essential significance on the functionality of the culture systems of the inventions. For example, a culture system consisting essentially of a basic medium and medium supplements will not include or will include only insignificant amounts (amounts that will have an insignificant effect on the propagation of cells in the culture system) of other substances that have an effect on cells in a culture. Also, a system consisting essentially of the elements as defined herein would not exclude trace contaminants. "Consisting of" shall mean excluding more than trace amounts of other elements. Embodiments defined by each of these transition terms are within the scope of this invention.

Further, all numerical values, e.g., concentration or dose or ranges thereof, are approximations which are varied (+) or (−) by up to 20%, at times by up to 10%, from the stated values. It is to be understood, even if not always explicitly stated that all numerical designations are preceded by the term "about". It also is to be understood, although not always explicitly stated, that the reagents described herein are merely exemplary and that equivalents of such are known in the art.

In its broadest sense, the present invention concerns culture systems and methods for the maintenance and preferably propagation of undifferentiated, pluripotent stem cells (SCs) in suspension. The culture system provided herein has been found to be especially suitable for large scale and long term maintenance of undifferentiated stem cells.

GLOSSARY

In the following description and claims use will be made, at times, with a variety of terms, and the meaning of such terms as they should be construed in accordance with the invention is as follows:

"Stem cells", as used herein, refers to cells which under suitable conditions are capable of differentiating into other cell types having a particular, specialized function (i.e., "fully differentiated" cells) while under other suitable conditions are capable of self renewing and remaining in an undifferentiated pluripotential state as detailed below. A "cell" as used herein refers to a single cell as well as to a population of (i.e. more than one) cells. The population may be a pure population comprising one cell type. Alternatively, the population may comprise more than one cell type. The stem cells are preferably hematopoietic stem cells obtained from bone marrow tissue of an individual at any age or from cord blood of a newborn individual, embryonic stem (ES) cells obtained from the embryonic tissue formed after gestation (e.g., blastocyst), or embryonic germ (EG) cells obtained from the genital tissue of a fetus any time during gestation, preferably before 10 weeks of gestation.

"Embryonic stem cell" and "Pluripotent embryonic stem cell", as used herein, refer to a cell which can give rise to many differentiated cell types in an embryo or an adult, including the germ cells (sperm and eggs). This cell type is also referred to as an "ES" cell.

"Cell culture" or "Cultured cell", as used herein, refer to cells or tissues that are maintained, cultured, cultivated or grown in an artificial, in vitro environment. Included within this term are continuous cell lines (e.g. with an immortal phenotype), primary cell cultures, finite cell lines (e.g., non-transformed cells), and any other cell population maintained in vitro. In this connection, a primary cell is a cell which is directly obtained from a tissue or organ of an animal, including a human, in the absence of culture. Typically, though not necessarily, a primary cell is capable of undergoing ten or fewer passages in vitro before senescence and/or cessation of proliferation.

"Undifferentiated pluripotential ES cells", "Pluripotent SC", and "ESC", as used herein, refer to precursor cells that have the ability to form any adult cell. Such cells are true cell lines in that they: (i) are capable of indefinite proliferation in vitro in an undifferentiated state; and (ii) are capable of differentiation to derivatives of all three embryonic germ layers (endoderm, mesoderm, and ectoderm) even after prolonged culture. Human ES cells (hES cells) are derived from fertilized embryos that are less than one week old (in the cleavage or blastocyte stage) or produced by artificial means (such as by nuclear transfer) that have equivalent characteristics.

"Undifferentiated", as used herein, refers to cultured cells when a substantial proportion (at least 20%, and possibly over 50% or 80%) of the cells and their derivatives in the population display morphological characteristics of undifferentiated cells, distinguishing them from differentiated cells of embryo or adult origin. Cells are recognized as proliferating in an undifferentiated state when they go through at least 1 population doubling during a cultivation period of at least 3 weeks, while retaining at least about 50%, or the same proportion of cells bearing characteristic markers or morphological characteristics of undifferentiated cells after said cultivation period.

"Maintenance" means continued survival of a cell or population of cells, at times, with an increase in numbers of cells. "Proliferation", "propagation", "expansion" and "growth", which may be used interchangeably with each other, refer to such an increase in cell number. According to one embodiment, this term refers to a continuous survival of the cells for at least 6 weeks, preferably for at least 10 weeks.

"Cell suspension" as used herein, refers to a culture of cells in which the majority of the cells freely float in the medium, typically a culture medium (system), and the cells floating as single cells, as cell clusters and/or as cell aggregates. In other words, the cells survive and propagate in the medium without being attached to a substrate.

"Culture system", as used herein, refers to a culture system suitable for the propagation of SCs. The term denotes a combination of elements, at minimum including a basic medium (a cell culture medium usually comprising a defined base solution, which includes salts, sugars and amino acids) and the serum replacement supplement KOSR. The culture system in accordance with the invention may further comprise other elements such as, without being limited thereto, an extracellular matrix (ECM) component, a serum or serum replacement (in addition to KOSR), a culture (nutrient) medium and other exogenously added factors, which together provide suitable conditions that support SC growth. The conditions are such that SC can proceed through the cell cycle, grow and divide. Preferably, the conditions are such which enable growth of human stem cells, preferably, human embryonic stem cells (hESC). Further, the culture system provides conditions that permit the SC to stably proliferate in the culture system for at least 6 weeks. It is intended that the definition encompass outgrowth as well as maintenance media.

"Large scale", as used herein with regard to cell cultivation and expansion, refers to the cultivation of SC under conditions which permit at least the doubling of cells after 4 weeks. The term may be used to denote cultures of both undifferentiated pluripotent stem cells and cultures of differentiated cells derived from stem cells (either by directed differentiation or by spontaneous differentiation).

"Long term" as used herein with regard to cell cultivation and expansion, refers to the cultivation of SC for at least X weeks, preferably, for at least 6 weeks and more preferably, for at least 10 weeks.

"Laminin-free culture system" refers to any culture system which has not been supplemented with laminin or laminin equivalent which being capable of providing culture conditions for the maintenance and/or expansion of stem cells.

"Cell marker", as used herein, refers to is any phenotypic feature of a cell that can be used to characterize it or discriminate it from other cell types. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the cell type of interest. The markers can also be identified by a biochemical or enzyme assay that depends on the function of the gene product. Associated with each marker is the gene that encodes the transcript, and the events that lead to marker expression. A marker is said to be preferentially expressed in an undifferentiated or differentiated cell population, if it is expressed at a level that is at least 5 times higher (in terms of total gene product measured in an antibody or PCR assay) or 5 times more frequently (in terms of positive cells in the population). Markers that are expressed 10, 100, or 10,000 times higher or more frequently are increasingly more preferred.

"Culture systems that supports differentiation into selected population of somatic cells", as used herein, refers to a variety of culture systems known in the art to promote specific differentiation to a specifically desired population of somatic cells. For example, a culture system that supports the directed differentiation of SCs into neural precursor cells may comprise a basic medium supplemented by FGF2 and/or noggin, as described, for example by Itsykson, P., et al.[14]. Further, for example, a culture system that supports the directed differentiation into dopaminergic neuronal cells will initially comprise the same conditions supporting differentiation into neural precursor cells, the latter directed into dopaminergic neuronal cells by the supplementation of the medium with at least one of sonic hedgehog (SHH), fibroblast growth factor (FGF), or a member of the Wnt family[15].

"Culture conditions/systems that support spontaneous differentiation into somatic cells", as used herein, refers to any culture conditions that promoted spontaneous nonspecific differentiation of stem cells to a mixture of somatic cells from any of the three embryonic germ layers: ectoderm; mesoderm; and endoderm. The medium in such culture conditions will typically be without components known to be required for the maintenance of SCs in an undifferentiated (pluripotent) state. Such components typically include soluble factors typically added to media for maintenance of undifferentiated SCs. An example of a medium that supports spontaneous differentiation of SCs into somatic cells comprises a basic medium of DMEM supplemented by FCS 20%, as described by Reubinoff et al.[1].

(If you agree with the above corrections we need to correct it throughout the document)

In accordance with the broadest aspect, the present invention provides a culture system for expansion of SCs comprising a suspension of undifferentiated SCs within basic medium and knockout serum replacement (KOSR). As indicated above, it was surprisingly found that the combination of KOSR with a basic medium provided conditions suitable for the expansion of pluripotent SCs. The SCs were maintained in an undifferentiated state for a long period, i.e. of at least 6 weeks.

The culture system in accordance with the invention comprise the suspension wherein the SCs are in the form of free floating undifferentiated SCs, free floating clusters of undifferentiated SCs or free floating aggregates of undifferentiated SCs.

SCs can be obtained using well-known cell-culture methods. For example, hESC can be isolated from human blastocysts, morulas, cleavage stage embryos or blastomeres.

Human blastocysts are typically obtained from human pre-implantation embryos, from in vitro fertilized (IVF) embryos or parthenogenetically activated oocytes. Alternatively, a single cell human embryo can be expanded to the cleavage stage, morula or blastocyst stage. For the isolation of human ES cells from blastocysts, most commonly the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 1-2 weeks. For further details on methods of preparation human ES cells see Thomson et al. [U.S. Pat. No. 5,843,780; Science 282:1145, 1998; Curr. Top. Dev. Biol. 38:133, 1998; Proc. Natl. Acad. Sci. USA 92: 7844, 1995]; as well as Bongso et al. [Hum Reprod 4: 706, 1989]; Gardner et al. [Fertil. Steril. 69:84, 1998]; and Klimanskaya et al. [Nature. 446: 342, 2007].

Commercially available SCs can be also be used in accordance with the invention. hESCs can be purchased from the NIH human embryonic stem cells registry. Non-limiting examples of commercially available embryonic stem cell lines are BG01, BG02, BG03, BG04, CY12, CY30, CY92, CY10, TE03 and TE32.

Pluripotent SCs present at their surface, or express, biological markers which are used to identify pluripotent SCs as well as to verify that the cells in the culture are maintained in an undifferentiated state [Thomson J A et al. Embryonic Stem Cell Lines Derived from Human Blastocysts *Science* 282 (5391):1145-1147 (1998)]. A non-limiting list of such cell markers comprise stage-specific embryonic antigens such as SSEA-3 and SSEA-4; antibodies to specific extracellular matrix molecule which are synthesized by undifferentiated pluripotent SC, such as TRA-1-60, TRA-1-81, and GCTM-2; elevated expression of alkaline phosphatase, which is associated with undifferentiated pluripotent SCs; and transcription factors unique to pluripotent SCs and which are essential for establishment and maintenance of undifferentiated SCs, such as OCT-4, Nanog and Genesis [Carpenter, M. K., Rosler, E., Rao, M. S., Characterization and Differentiation of Human Embryonic Stem Cells. *Cloning and Stem Cells* 5, 79-88, 2003].

Generally, the basic medium may be any basic medium known in the art. In a preferred embodiment the basic medium is selected from Neurobasal™, Cellgro Stem Cell Growth Medium, KO-DMEM and X-Vivo 10. Most preferably the present invention makes use of Neurobasal™ as the basic medium (i.e. the basic media consists essentially of Neurobasal™). Neurobasal™ is known in the art of cell cultures [Brewer G J. Serum-free B27/Neurobasal medium supports differential growth of neurons from the striatum, substantia nigra, septum, cerebral cortex, *J Neurosci Res.* 42(5):674-83, (1995)] and is commercially available [Gibco, Invitrogen cell culture, USA].

The culture system, e.g. Neurobasal™ supplemented with KOSR, may be supplemented by other components known to be used in culture systems, comprising, without being limited thereto, a member of FGF family. In accordance with one embodiment, the FGF member is, without being limited thereto, FGF2.

The culture system may be further supplemented by an extracellular matrix (ECM) component. In accordance with one embodiment, the ECM is selected from, without being limited thereto, fibronectin, laminin and gelatin.

The culture system may be further supplemented by an antibacterial agent. The antibacterial agent may be selected from, without being limited thereto, penicillin and streptomycin.

The culture system may be further supplemented by non-essential amino acids (NEAA).

In addition, the culture system may be further supplemented by a TGFβ superfamily factor. The TGFβ superfamily factor may be, without being limited thereto, activin A.

The culture system may be further supplemented by a neurotrophin. Neutrophins are known to play a role in assisting to promote the survival of SCs in culture. In accordance with an embodiment of the invention, the neurotrophin is selected from, without being limited thereto, BDNF, NT3, NT4.

The culture system may be further supplemented by nicotinamide (NA). It is noted that NA may assist in preventing the differentiation of cells into extraembryonic lineages, maintaining them as undifferentiated cells, assist in promoting the cells' survival and proliferation.

The culture system may be further supplemented by a bone morphogenic protein (BMP) antagonist. It is noted that under culture conditions that support undifferentiated proliferation of hESCs noggin (a BMP antagonist) prevents extraembryonic background differentiation of hESCs. While under conditions that promote differentiation, noggin is known to prevent the differentiation to non-neural lineages, favoring the differentiation to a neural fate. The BMP antagonist may be selected from, without being limited thereto, noggin, chordin, or gremlin.

Further, the culture system may be supplemented by a serum free medium supplement. The serum free medium supplement is selected from, without being limited thereto, Nutridoma-CS or TCH™. Preferably the culture system is supplemented by Nutridoma-CS.

The culture system of the invention is preferably applicable for the expansion in a suspension of embryonic SCs. A further preferred embodiment of the invention encompasses the expansion in a suspension of human SCs.

A preferred embodiment of the invention comprises a culture system for the expansion of hESCs in an undifferentiated state, the hESCs being pluripotent stem cells. Most preferably, the invention provides a culture system for the expansion of hESCs, the culture system comprising a suspension of such cells in a medium comprising Neurobasal™ and KOSR, the culture system permitting expansion of the cells in an undifferentiated pluripotent state. In a preferred embodiment, the invention provides a culture system for the expansion of hESCs, the culture system comprising a suspension of such cells in a basic medium consisting of Neurobasal™ and the culture system comprising KOSR, the culture system permitting expansion of the cells in an undifferentiated pluripotent state.

The results presented hereinbelow also show that the culture system may be free of laminin. Laminin has been shown in culture to stimulate neurite outgrowth, promote cell attachment, chemotaxis, and cell differentiation. The present invention has found that when supplementing the basic media with a serum free medium supplement, e.g. Neutridoma CS, not only there is no need to add laminin but also, an increase number of cells was observed after a long term of cultivation in suspension, as compared to the number of cells outgrown in the presence of laminin.

The culture system of the invention is preferably suitable for long term expansion of SCs. In accordance with one embodiment, long term refers to at least six weeks of cultivation and cell expansion. During this term, the SCs exhibit cell markers which confirm that the SCs are essentially maintained in an undifferentiated pluripotent state.

It should be well appreciated by those versed in the art that a culture system in accordance with the invention, i.e. a culture system for the expansion of SCs in a suspension, wherein the SCs are maintained for a long period of time in an undifferentiated, pluripotent state, may be of significant benefit for large scale propagation of SCs in bioreactors. As well appreciated by those versed in the art, it is advantageous to provide conditions that allow for large scale production of standardized homogeneous undifferentiated hESCs. The advantages of suspension culture bioreactors were also described above, in particular for large scale expansion.

The invention also provides a method of expanding SCs in an undifferentiated state, the method comprising incubating undifferentiated SCs in suspension within a culture system comprising basic medium and knockout serum replacement (KOSR). Preferably, the method comprises incubating undifferentiated SCs in suspension within a culture system comprising basic medium consisting of Neurobasal™ and further comprising knockout serum replacement (KOSR).

The method of the invention also comprises the step of obtaining SCs from SC colonies cultivated on a feeder layer or in a feeder free adherent culture system. The SCs may be obtained by dissociation of the cells from the culture system, e.g. by the aid of suitable agents (e.g. collagenase IV), trituration and transferring the dissociated SCs into the culture system of the invention to form a suspension of SCs, the latter being in the form of free floating cells, free floating clusters of cells or free floating aggregates of cells.

The method may also comprise one or more media refreshment (i.e. the replacement of at least 50% of the culture system). It is appreciated that by said media refreshment, dead cells and their fragments are gradually removed. Culture media may be refreshed at least every 2-3 days, and most preferably at least every 2 days. The media refreshment may include the replacement of a portion of the basic media only, as well as the replacement of a portion of the basic media including one or more of its components. Further, it is appreciated that the method may comprise different media replacements, e.g. at times only the replacement of the basic medium, and at other time points, the replacement of the basic medium comprising one or more of the supplements.

It is also appreciated that as a result of cells expansion, the SCs may proliferate into big clusters. Thus, the method of the invention may also comprise one or more SCs manipulations so as to disaggregate the big clusters of cells resulting from their overgrowth. According to one embodiment, the overgrowth of the cells in clusters is prevented by trituration. The essentially disaggregated cells may then be transferred to suitable tissue culture carriers (e.g. dishes, culture tubes, culture bioreactors, etc.) for continued expansion. Overgrowth of clusters may be prevented by other means such as chopping the clusters or the use of increased shearing forces of bioreactor systems or any other method known in the art.

It has been found that the undifferentiated and pluripotent SCs obtained using the culture system of the invention may be, at any stage of expansion, induced to differentiate into a variety of somatic cells from the three embryonic major lineages; endoderm, ectoderm and mesoderm.

Depending on the type of culture system used for the induction of differentiation, the nature of the resulting population may be a priori determined.

In accordance with one embodiment, the undifferentiated and pluripotent SCs are induced to differentiate into a specific and pre-selected fate. In other words, the undifferentiated and pluripotent SCs are cultivated in a culture system that directs differentiation to a specific somatic cells, thereby providing a population of cells highly enriched for a specific cell type or a pure population of cells of a single type. A variety of single type somatic cell populations may be derived from undifferentiated and pluripotent SCs and those versed in the art will know how to select the medium components and establish the culture system which direct the specific differentiation of the latter to the desired population of somatic cells.

For example, directing differentiation of undifferentiated and pluripotent SCs to neural precursor cells may be obtained by cultivating the SCs in a culture system comprising DMEM/F12 medium (Gibco) supplemented with B27 (1%, Gibco) (DMEM/F12/B27 medium), FGF-2 (20 ng/ml) and noggin (750 ng/m, R&D Systems, Inc., Minneapolis, Minn.) as exemplified hereinbelow and also by Itsykson, P., et al.[14]) or by Reubinoff et al.[(24)].

Further, for example, directing differentiation of SCs to midbrain dopamineric neuronal cells may be obtained by first by inducing differentiation into neural precursor cells, such as described above, followed by cultivation in a basic medium, such as DMEM/F12/B27 medium supplemented with at least one of fibroblast growth factor 8 (FGF8) and sonic hedgehog (SHH), a member of the Wnt family, as exemplified below and also described by Yan, Y. et al.[15]. Co-culture with cells that promote midbrain differentiation such as the PA6 stromal cells, or midbrain astrocytes may be also used.

In accordance with another embodiment, the SCs may be induced for spontaneous non-specific differentiation of somatic cells. This may be achieved, for example, by the use of a culture media that is free of soluble factors and/or ECM components typically used for maintaining SCs in undifferentiated state, the exclusion thereof from the culture media is known to promote spontaneous differentiation of SCs, as also described by Itsykson, P., et al.[(14)] Reubinoff et al [Nat Biotechnol 18, 399-404 (2000)].

In accordance with this embodiment, within the culture system the undifferentiated pluripotent SCs (in suspension) are induced to form embryoid bodies (EBs). The said EBs are disaggregated and further plated and cultured in the same medium of the EBs. It is noted that the production of a mixture of non-specific somatic cells was exhibited by expression of human muscle actin, indicating the presence of mesodermal cells in the cell culture; or by expression of Sox-17, indicating the presence of endodermal cells in the cell culture.

Methods other than spontaneous differentiation within EBs may be used to derive somatic cells for example differentiation in flat culture; and other culture systems may be used to promote differentiation towards specific cell types[(26, 27)]

It is noted that the undifferentiated pluripotent SCs of the invention may also be used for the production of Teratoma tumors. This may be achieved by injection of the pluripotent SCs into an animal.

As indicated above, the culture system of the invention is especially suitable for large scale production of SCs. Thus, it should be appreciated that the methods of the invention for the production of specific as well as non-specific somatic cells, making use of the SCs produced using the culture system of the invention, are also suitable for large scale production of such somatic cells. In other words, the present invention provides methods for the large scale production of SCs as well as for the large scale production of somatic cells derived therefrom (either by spontaneous or directed differentiation).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art.

All publications, patents and patent applications mentioned in this specification are herein incorporated in their entirety by reference into the specification.

The invention will now be described with reference to the following non-limiting examples.

SOME EXEMPLARY EMBODIMENTS

Materials and Methods
Human Feeders and Preparation of Feeder Layers

Foreskin cells from an established line were used as feeders as previously described (Banin E, Obolensky A, Idelson M, Hemo I, Reinhardtz E, Pikarsky E, Ben-Hur T, Reubinoff B. Retinal incorporation and differentiation of neural precursors derived from human embryonic stem cells. Stem Cells 2006; 24(2): 246-57). Briefly, the foreskin fibroblasts were cultured in DMEM (Gibco, Gaithersburg, Md.) supplemented with 10% Fetal Calf Serum (FCS) (Biological Industries, Beit Haemek, Israel). They were passaged by trypsin (Gibco) digestion. For the preparation of feeder layers $3 \times 10^5$ cells were plated per well of a six well plate (Corning, N.Y., USA), precoated with 0.1% gelatin (Sigma, St. Louis, Mo.). Mitotic inactivation of the feeders was carried out prior to plating by incubating them 2.5 hours with Mitomycin-C 5 µg/ml (Kyowa, Tokyo).

hESC Culture System hESCs were cultured on the human feeder layers in KO medium (KOM) consisting of 85% KO-DMEM, 15% KOSR, 1 mM glutamine, 0.1 mM β-mercaptoethanol, 1% nonessential amino acids, 50 units/ml penicillin, 50 µg/ml streptomycin, (Gibco, Gaithersburg, Md.) and 4 ng/ml FGF-2 (R&D Systems, Inc., Minneapolis, Minn.). hESCs were weekly passaged with Ca/Mg$^{++}$-free PBS supplemented with 0.05% EDTA (Biological Industries, Beit Haemek, Israel) or type IV collagenase (1 mg/ml; Gibco) and plated onto fresh feeder layer.

Suspension Culture of hESC hESC colonies that were cultivated on human feeders in the KO culture system described above and in WO 2006/070370, the entire contents of which is specifically incorporated herein by reference, were firstly dissociated with the aid of collagenase IV (1 mg/ml, 2-3 hours at 37°). Cell dissociation was promoted by agitation of the culture plate. The cell clusters obtained were resuspended in fresh NBSR medium (Neurobasal™, 14% KOSR, glutamine 2 mM, 50 units/ml penicillin, 50 µg/ml streptomycin, 1% nonessential amino acids; Gibco), or where indicated in fresh NBN2 medium (Neurobasal™, N2 supplement 1:100, glutamine 2 mM, 50 units/ml penicillin, 50 µg/ml streptomycin). Both media were supplemented with FGF-2 20 ng/ml, activin 25 ng/ml, fibronectin and laminin 5 µg/ml each, gelatin 0.001%, and BDNF, NT3 and NT4, 10 ng/ml each.

When indicated, cell clusters were resuspended in NBSR medium supplemented with 1× Nutridoma-CS (Roche, Germany), FGF-2 20 ng/ml, activin 25-50 ng/ml, fibronectin 5 µg/ml, and gelatin 0.001%, with and without laminin 5 µg/ml.

The suspension was either strained though 30-50 micron mesh to remove big clumps, or triturated by pipetting to disaggregate big clumps and transferred into tissue culture dishes (Costar®, Corning Inc., Corning, N.Y.) at a density of $0.7-1.2 \times 10^6$ cells/ml. Dead cells and their fragments were gradually removed during media refreshment every two days. The cells proliferated as free-floating tiny transparent clusters of 20-50 cells. Aggregation and overgrowth of clusters was prevented by trituration with a 1000 µl pipettor tip as required.

Characterization of hESC Grown in Suspension by FACS Analysis

For characterization of the cells within the small free-floating aggregates, hESCs were dissociated with a solution of 2.25 mM EDTA with 0.06% trypsin, for 7-10 min at 37°, followed by gentle trituration, to obtain a single-cell suspension solution.

The hESC were then washed with FACS media consisting of PBS supplemented with 1% BSA and 0.05% sodium azide. The single-cell suspension was stained with anti-SSEA4 (1:100, mouse monoclonal IgG3, Developmental Studies Hybridoma Bank (DHSB), Iowa City, Iowa), anti-Tra-1-60 (1:100, monoclonal mouse IgM, Chemicon International), and anti-Tra-1-81 (1:100, monoclonal mouse IgM, Chemicon International). Control hESCs were stained with their respective isotype control antibodies. Primary antibodies were detected using fluorescein isothiocyanate (FITC)-labeled goat anti-mouse Ig (1:100, Dako). Propidium iodide (PI) was added (final concentration of 4 µg/ml) for better gating of viable cells. FACS analysis was performed using the FACS-Calibur system (Becton-Dickinson, San Jose, Calif.).

Replating and Monolayer Culture of hESCs Cultivated in Suspension

Floating aggregates of hESCs were triturated with a 1000 µl pipettor tip. Tiny clusters that were obtained were plated on fresh feeders and cultured in KOSR medium (as above) supplemented with 4 ng/ml FGF2. After 1 week, colonies with typical morphological characteristics of the colonies of undifferentiated hESCs, developed on the feeders. These colonies could be passaged routinely as described before. Alkaline phosphatase activity of the cells within the plated colonies was demonstrated using the Alkaline Phosphatase Substrate kit I by Vector Laboratories (Burlingame, Calif.) according to the manufacturer's instructions.

EB Formation

The clusters of undifferentiated hESCs were transferred and cultured for 3-4 weeks in DMEM (Gibco), supplemented with 20% FBS (Biological Industries, Beit Haemek), 1 mM L-glutamine, 0.1 mM β-mercaptoethanol, 1% non-essential amino acid stock, 50 units/ml penicillin, 50 µg/ml streptomycin (all from Gibco Invitrogen Corporation products, USA).

Induction of Somatic Differentiation and Immunohistochemistry

Clusters of undifferentiated hESCs were transferred and cultured for 2-3 weeks in suspension within bacteriological dishes precoated with 0.1% low melting temperature agarose in DMEM/F12 medium (Gibco) supplemented with B27 (1%, Gibco) (DMEM/F12/B27 medium), FGF-2 (20 ng/ml) and noggin (750 ng/m, R&D Systems, Inc., Minneapolis, Minn.).

Clumps of neural precursors were triturated to small clusters and plated on poly-D-lysine (30-70 kDa, 10 µg/ml; Sigma, St. Louis, Mo.) and laminin-coated (4 µg/ml; Sigma) glass coverslips and cultured for an additional week with DMEM/F12/B27 medium in the absence of growth factors.

In addition, to promote differentiation to midbrain dopaminergic neurons, clumps of neural precursors were triturated to small clusters and plated on poly-D-lysine and laminin-coated glass coverslips (as above) and cultured for 2 weeks with DMEM/F12/B27 medium supplemented with FGF8 and SHH.

EBs were dissociated with the aid of trypsin (0.025%, 3 mM EDTA in PBS) digestion, and plated on poly-D-lysine and laminin pre-coated glass coverslips (as above) and cultured for additional 1-2 weeks in the culture medium used for induction of differentiation of EBs.

Differentiated cells within the outgrowth were fixed with 4% paraformaldehyde for 20 minutes at room temperature. Cell membranes were permeabilized with 0.2% Triton X100 (Sigma) in PBS for 5 minutes for immunostaining with anti-intracellular marker antibodies. Neural precursors were incubated with the following primary antibodies: anti-β-III-tubulin (mouse monoclonal IgG2b, 1:2000, Sigma), anti-rabbit TH (1:200, Pel Freeze), and anti-mouse EN-1 (1:100, Developmental Studies Hybridoma Bank (DHSB), Iowa City, Iowa). Mesodermal differentiation within EBs' outgrowth was detected with the antibody against human muscle actin (1:50, DAKO). Endodermal differentiation within EBs' outgrowth was detected with the antibody against Sox-17 (1:50, R&D Systems Inc.). Primary antibody localization was performed by using fluorescein isothiocyanate (FITC)-conjugated goat anti-rabbit immunoglobulins (Dako, 1:20-50), or goat anti-mouse immunoglobulin conjugated with Cy3 (1:500 Jackson ImmunoResearch Laboratories).

Teratoma Formation in NOD/SCID Mice

Clumps of hESCs that were propagated for 7 weeks in suspension were injected into the testis of six weeks old NOD/SCID mice (Harlan, Jerusalem, Ill.) (30-40 clumps per testis). Eight to twelve weeks later, the resulting tumors were removed, embedded in paraffin and sections were stained with H&E.

Results

NBSR Suspension Culture System for the Propagation of hESC in Bulk

To develop suspension cultures, hESC colonies that were cultivated on human feeders in the KO culture system were dissociated with the aid of type IV collagenase. The cells/cell clusters that were obtained were re-suspended within fresh NBSR medium, supplemented with FGFs (FGF-2 20 ng/ml).

Further supplementation of the medium with one or more of the following components increased the survival/proliferation and prevented differentiation of the cells:

TGFβ superfamily factors (e.g., activin 25-50 ng/ml)
ECM components (e.g., laminin 5 µg/ml, fibronectin 5 µg/ml, gelatin 0.001%)
Neurotrophins (e.g., NT4, NT4, BDNF 10 ng/ml each)

Figure 2:
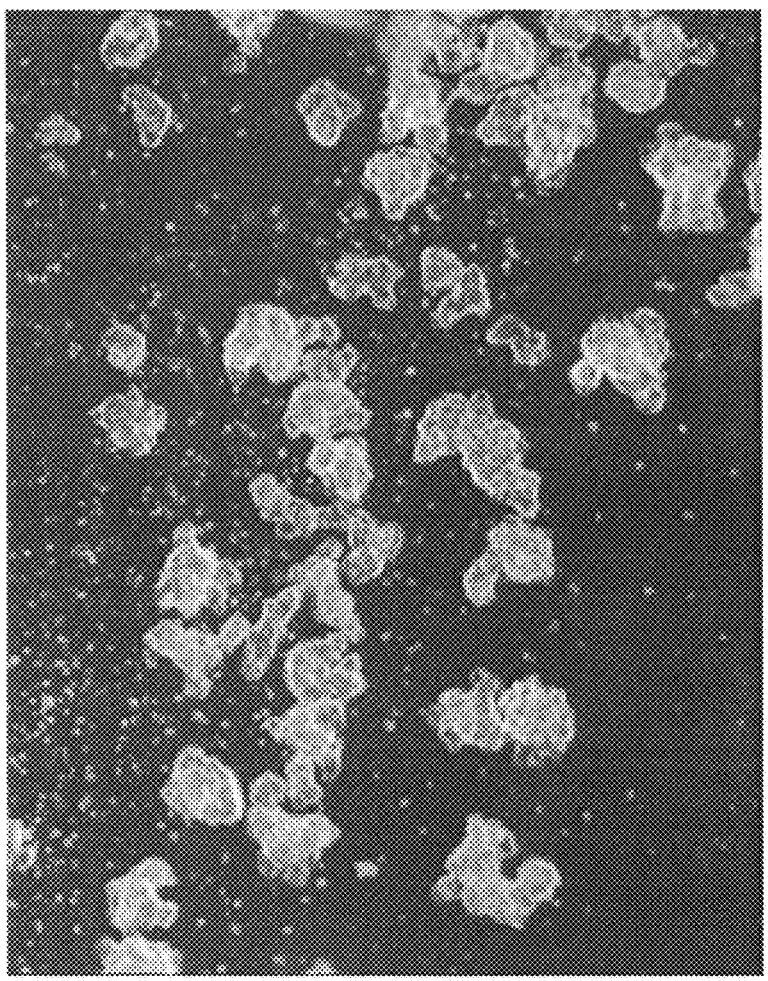
FIG. 2: is a dark field micrograph of undifferentiated hESCs in a suspension cultures in NB medium supplemented with KOSR.

The cells were transferred to suspension at a density of ~0.7-1.2×10$^6$ cells/ml. Dead/fragmented cells were gradually removed during medium refreshment. The cells proliferate as free-floating tiny transparent clusters of 20-50 cells without any morphological signs of differentiation (FIG. 2). Aggregation and overgrowth of the transparent clusters were prevented by trituration through a 1000 µl pipette tip as required. The hESCs grown in a suspension comprising Neurobasal™ medium supplemented with KOSR (NBSR) were sub-cultured by mechanical disaggregation.

The cells expressed SSEA4, TRA1-60, and TRA1-81 (markers of pluripotency), and did not express markers of somatic differentiation such as the neural marker PSA-NCAM. Specifically, after 3 weeks of cultivation in suspension under these culture conditions, >90% of the cells expressed SSEA4, TRA1-60, and TRA1-81 but not PSA-NCAM (FIGS. 3A-3E).

When re-plated on human feeders, after 3 and 7 weeks of suspension culture, the cells gave rise to monolayer colonies with the morphology of undifferentiated hESCs (FIG. 4A). The stem cells within these colonies expressed alkaline phosphatase (a marker used to identify stem cells; FIG. 4B).

It was concluded that efficient propagation of undifferentiated hESC in suspension is achievable using the unique combination of Neurobasal™ medium as the basic medium of the culture system, supplemented with KOSR (NBSR).

Suspension in NBSR was shown to be more effective than suspension in NBN2 (Neurobasal™ supplemented with N2) for the expansion of hESCs without differentiation. Specifically, after 3 weeks, the total number of cells in each of the cell cultures (NBSR vs. NBN2) was determined using trypan blue to include only live cells and hESCs propagated in NBSR reached a population of approximately double that of NBN2-cultured hESCs (FIG. 1).

Figure 5:
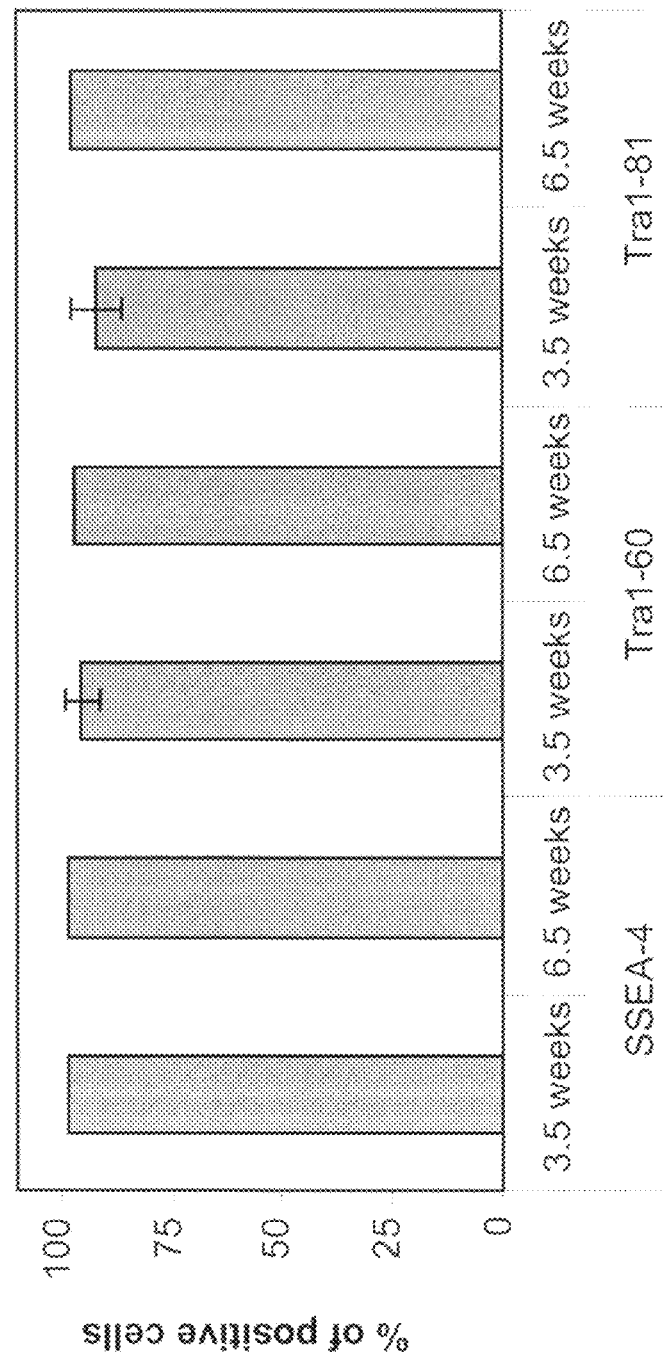
FIG. 5: is a bar graph showing that supplementation of NB with Nutridoma-CS, FGF2, activin A, ECM components and neutrophins promote long term propagation of undifferentiated hESC clusters in suspension, as exhibited in corresponding FACS analysis that showed that the percentage of hESCs expressing SSEA-4, TRA1-60, and TRA1-81 was high (>95%) and stable after 3.5 and 6.5 weeks of suspension culture.
Figure 12:
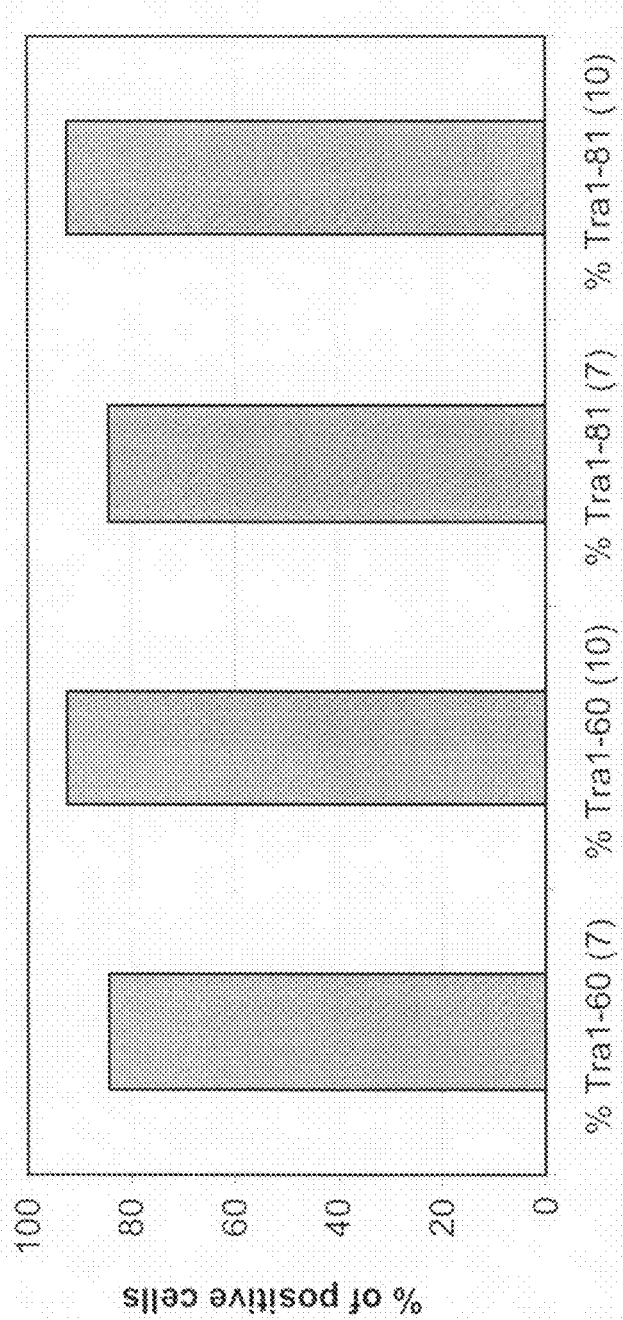
FIG. 12: is a bar graph showing that NB with Nutridoma-CS, FGF2, activin A, ECM components and neutrophins promotes long-term propagation of clusters of undifferentiated hESCs in suspension, as exhibited in corresponding FACS analysis, which showed that the percentage of hESCs expressing TRA1-60 and TRA1-81 was high and stable after 7 and 10 weeks of suspension culture.

NBSR medium that was supplemented with Nutridoma-CS, FGF-2, activin, ECM components (fibronectin, gelatin and laminin), and neutrophins could effectively support long-term cultivation of undifferentiated hESCs. The percentage of hESCs expressing markers of pluripotent stem cells (SSEA4, TRA1-60, and TRA1-81) was high (>95%) and stable after 3.5 weeks and 6.5 weeks of suspension culture (FIG. 5) as well as after 7 and 10 weeks (FIG. 12).

Figure 6:
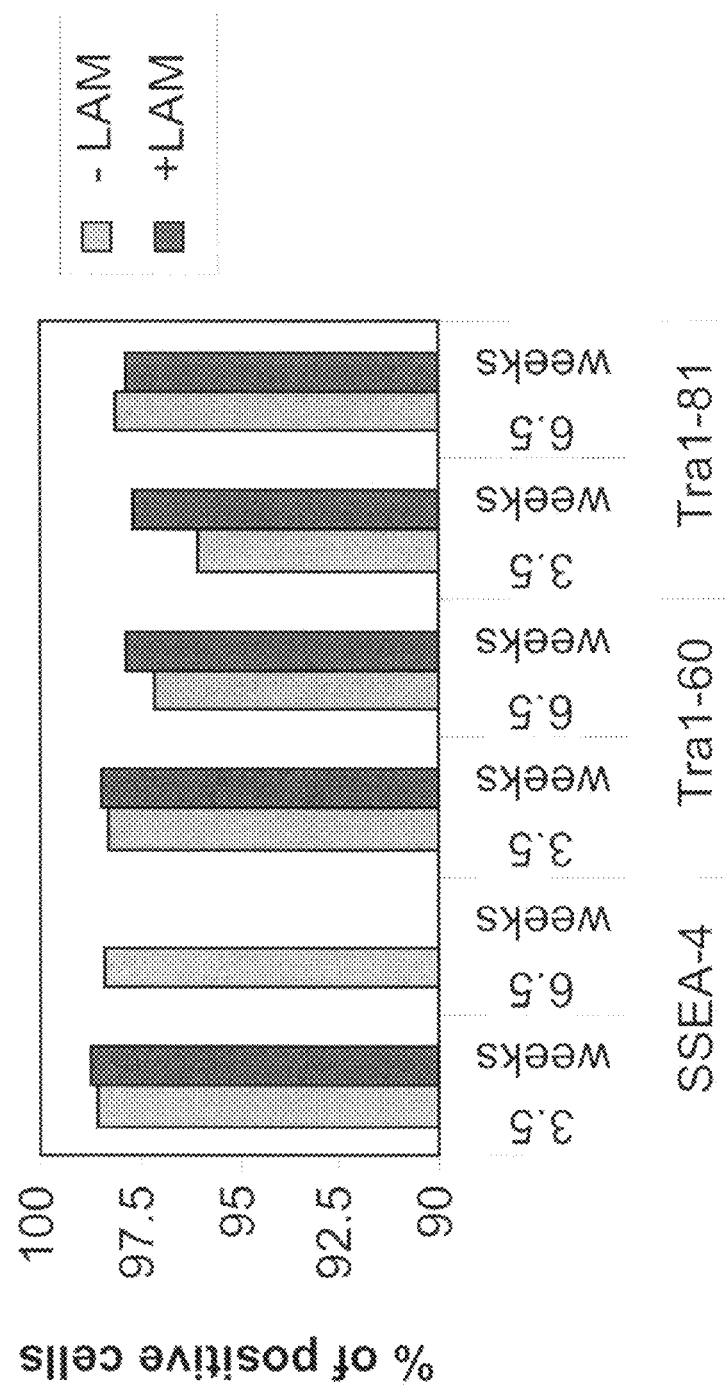
FIG. 6: is a bar graph showing that supplementation of NB Nutridoma-CS however, without laminin also promotes long term propagation of undifferentiated hESC clusters in suspension, as exhibited by the expression of the different markers (% positive cells) in the presence or absence of laminin (+LAM and −LAM, respectively) and after 3.5 and 6.5 weeks of suspension culture.
Figure 7:
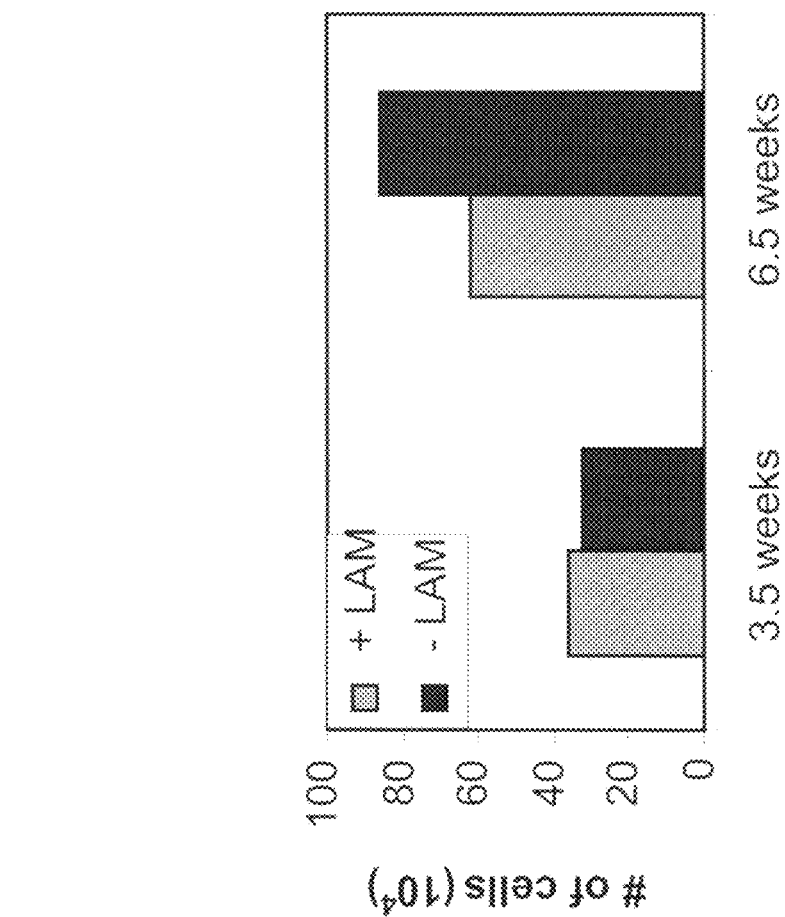
FIG. 7: is a bar graph showing the number of cells after long term suspension culture in NBSR supplemented with Nutridoma-CS being increased after 6.5 weeks in the absence (−LAM) as compared to the presence (+LAM) of laminin supplementation.

Furthermore, NBSR medium supplemented with Nutridoma-CS did not require the addition of laminin. Using the same supplementation as described above, however, with or without laminin showed that the percentage of undifferentiated cells cultured in NBSR/Nutridoma-CS was not significantly different in laminin-positive cultures (+LAM) versus cultures in which laminin was not added (−LAM) (FIG. 6). All the more and quite surprisingly, in the absence of laminin, an increased number of cells was observed after long-term cultivation (6.5 weeks) in the above described NBSR/Nutridoma-CS culture suspension (FIG. 7).

Induced Differentiation of hESCs Into Somatic Cells In Vitro

Undifferentiated hESCs that were cultivated in suspension within NBSR gave rise upon differentiation to somatic progeny.

Figure 8B:
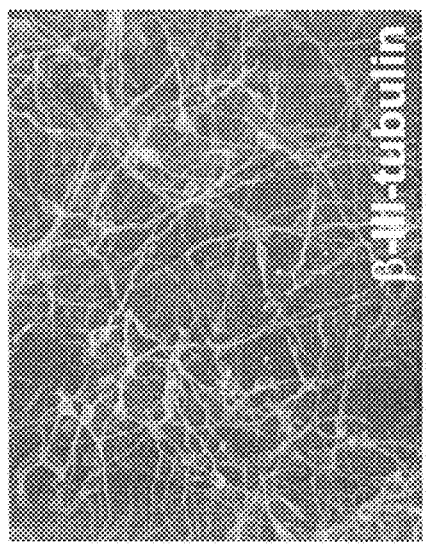
FIGS. 8A-8C: are phase contrast image (FIG. 8A), indirect immuno-fluorescence staining image (FIG. 8B) and image of nuclei counterstaining with DAPI (FIG. 8C) showing cells with morphological characteristics of neurons emanating from the clusters after induction in DMEM/F12 supplemented with B27, noggin and FGF2 for 2-3 weeks and culturing for a week on laminin coated slides.
Figure 8C:
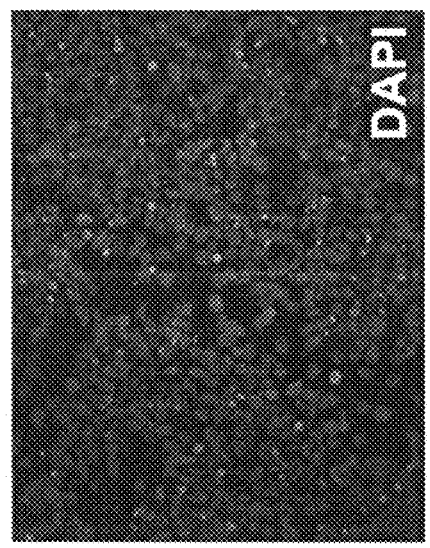
Figure 8A:
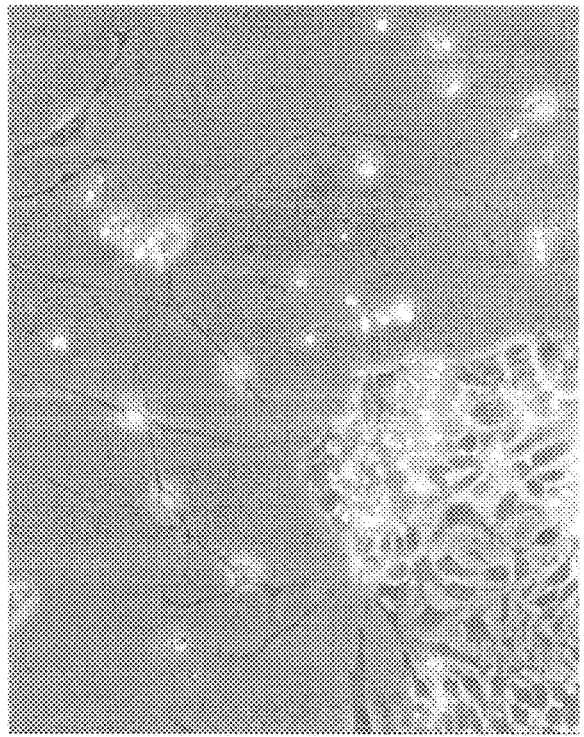
Figure 9:
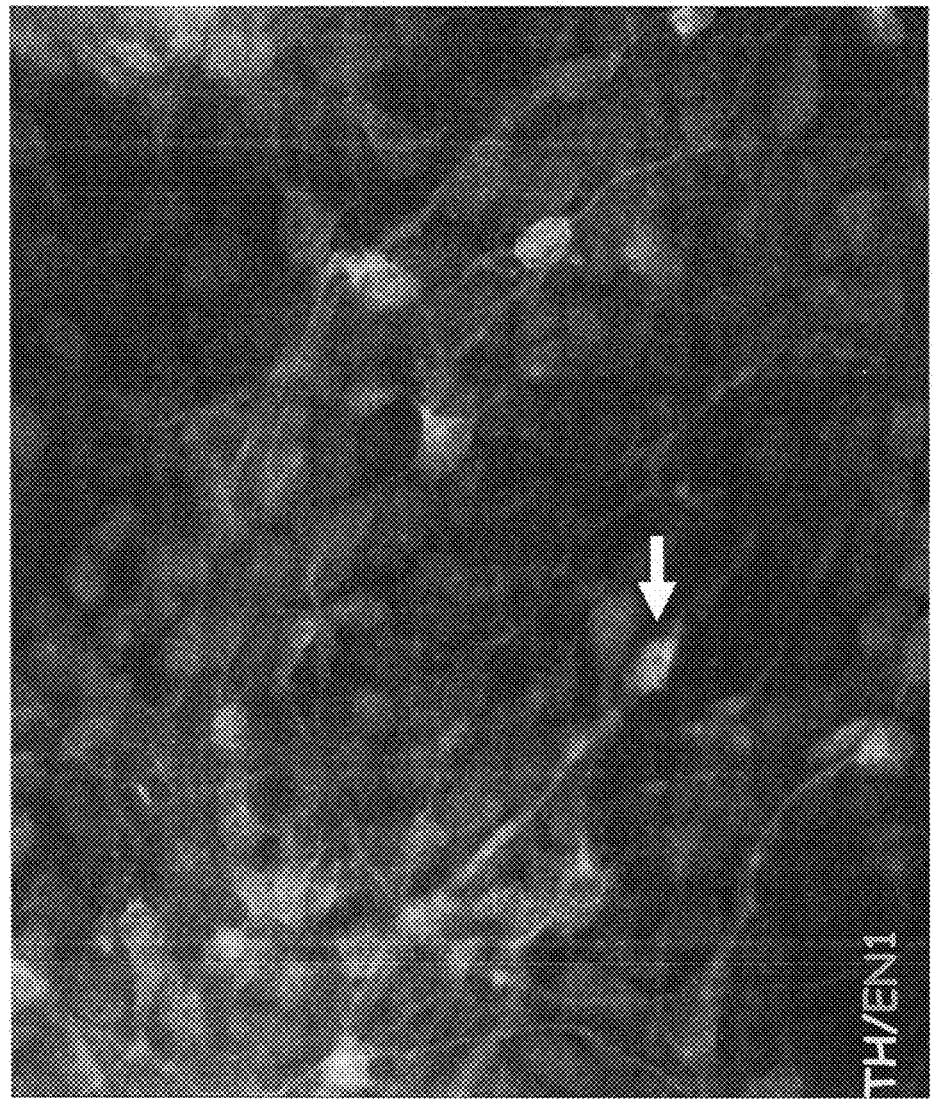
FIG. 9: is an immuno-fluorescent image showing that hESCs that were propagated in suspension could give rise to midbrain dopaminergic neurons co-expressing TH (light gray) and EN-1 (dark gray); The arrow shows a cell which co-expresses EN-1 and TH, after plating the hESCs on laminin coated slides and culturing in the presence of FGF8 and SHH for 2 weeks.

To induce neural differentiation the clusters were transferred and cultured for 2 weeks in DMEM/F12 supplemented with B27 (1%), FGF-2 (20 ng/ml) and noggin (750 ng/ml). These culture conditions had been previously demonstrated to be highly efficient for induction of neural differentiation of hESCs[14]. The clusters were then plated on laminin-coated slides and cultured for a week in the same medium in the absence of growth factors. Cells with morphological characteristics of neurons (FIG. 8A) gradually migrated from the clusters. Immunostaining demonstrated that these cells expressed the neuronal marker β-III-tubulin (FIG. 8B). When the clusters were plated on laminin coated slides for 2 weeks of differentiation in the presence of FGF8 and SHH (which promote differentiation toward a midbrain dopaminergic neuronal fate), multiple neurons co-expressing enlgraid-1 (EN-1) and tyrosine hydroxylase (TH) were observed (FIG. 9). The co-expression of these markers is characteristic of midbrain dopaminergic neurons[15]. The arrow shows a cell which co-expresses EN-1 and TH. The arrow is hard to see on the B/W figure. On the B/W scale, TH is indicated by light gray, and EN-1 is indicated by darker gray.

Figure 10:
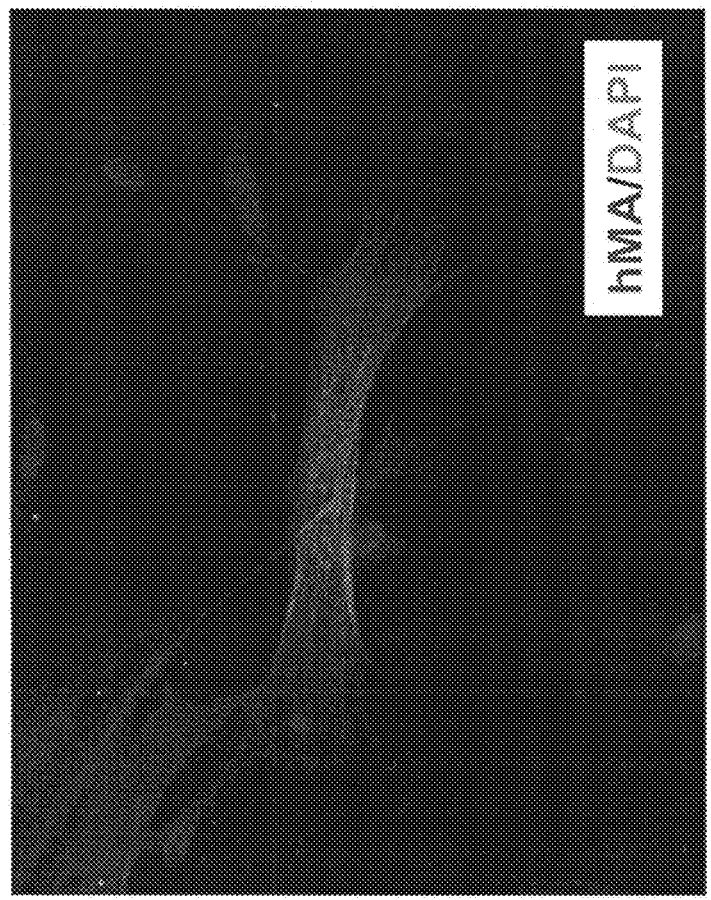
FIG. 10: is an immuno-fluorescent image showing that hESCs that were propagated in suspension could give rise to mesodermal cells expressing human muscle actin (hMA).
Figure 11:
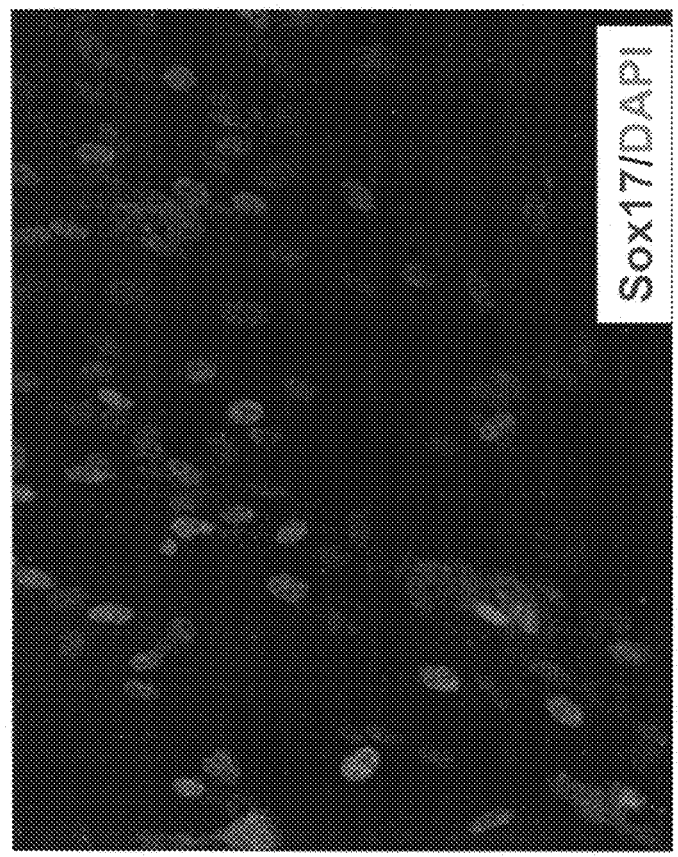
FIG. 11: is an immunofluorescent image showing that hESCs that were propagated in suspension could give rise to endodermal cells expressing Sox17.

To induce mesodermal and endodermal differentiation the clusters were transferred to DMEM supplemented with 20% FBS where they formed embryoid bodies (EBs). After 3-4 weeks of differentiation the EBs were dissociated, plated and cultured for 1-2 weeks on laminin coated coverslips. Immunostaining showed differentiated cells expressing muscle actin (mesoderm; FIG. 10), and Sox 17 (endoderm; FIG. 11).

To further demonstrate that the hESCs retained their pluripotent potential after cultivation in suspension, clusters of hESCs that were cultured in suspension for 7 weeks were injected into the testis of NOD/SCID mice. Teratoma tumors were removed after 8 weeks and histological analysis of the tumors demonstrated differentiated progeny of the three embryonic germ layers (FIGS. 13A-13C). Formation of teratoma is a key feature of hESCs and is an important evidence that the cells that grow in suspension are indeed pluripotent cells.

The invention claimed is:

1. A method of expanding human pluripotent stem cells (SCs), the method comprising
   incubating human pluripotent SCs in suspension within a culture system comprising basic medium, a knockout serum replacement (KOSR) and a TGFβ superfamily factor,
   wherein the human pluripotent SCs do not undergo differentiation during the expansion.

2. The method of claim 1, wherein the human pluripotent SCs are derived from human pluripotent SC colonies cultivated on a feeder layer or in a feeder free adherent culture system.

3. The method of claim 1, wherein the suspension of human pluripotent SCs comprises free floating cells, free floating clusters of cells or free floating aggregates of cells.

4. The method of claim 1, wherein the basic medium has the following composition:

|  | Concentration in uM |
| --- | --- |
| $CaCl_3$ (anhydrous) | 1800 |
| $FE(N_3O)_3 9H_2O$ | 0.2 |
| KCl | 5360 |
| $MgCl_3$ (anhydrous) | 812 |
| NaCl | 76000 |
| $NaHCO_3$ | 880 |
| $NaH_2PO_4 H_2O$ | 900 |
| $ZnSO_4 7H_2O$ | 0.67 |
| D-glucose | 25000 |
| phenol red | 23 |
| MOPS | 10000 |
| sodium pyruvate | 230 |
| L-alanine | 20 |
| L-arginine HCl | 400 |
| L-asparagine $H_2O$ | 5 |
| L-cysteine | 10 |
| L-glutamine | 500 |
| Glycine | 400 |
| L-histidine HCl $H_2O$ | 200 |
| L-isoleucine | 800 |
| L-leucine | 800 |
| L-lysine HCl | 5 |
| L-methionine | 200 |
| L-phenylalanine | 400 |
| L-proline | 67 |
| L-serine | 400 |
| L-threonine | 800 |
| L-tryptophan | 80 |
| L-tyrosine | 400 |
| L-valine | 800 |
| D-Ca pantothenate | 8 |
| choline chloride | 80 |
| folic acid | 8 |
| i-inositol | 40 |
| niacinamide | 30 |
| pyridoxal HCl | 20 |
| riboflavin | 1 |
| thiamine HCl | 10 |
| vitamin B12 | 0.2. |

5. The method of claim 1, wherein the culture system further comprises one or more element selected from the group consisting of a member of the FGF family, an extracellular matrix (ECM) component, an antibacterial agent, a non-essential amino acid, a neurotrophin, nicotinamide (NA), a bone morphogenic protein (BMP) antagonist and a serum free medium supplement.

6. The method of claim 5, wherein the ECM is selected from the group consisting of fibronectin, laminin and gelatin; the antibacterial agent is selected from the group consisting of penicillin and streptomycin; the TGFβ superfamily factor is activin A; the BMP antagonist is selected from the group consisting of noggin, chordin and gremlin; the neurotrophin is selected from the group consisting of BDNF, NT3 and NT4; and the serum free medium supplement is Nutridoma-CS.

7. The method of claim 1, wherein the human pluripotent SCs comprise human embryonic stem cells (hESCs).

8. The method of claim 1, wherein the expanding is effected in a bioreactor.

9. A culture system comprising a suspension of human pluripotent stem cells (SCs) in a culture medium comprising a basic medium, knockout serum replacement (KOSR), and a TGFβ superfamily factor.

10. The culture system of claim 9 wherein the suspension of human pluripotent stem cells comprises free floating cells, free floating clusters of cells or free floating aggregates of cells.

11. The culture system of claim 9, wherein the basic medium has the following composition:

|  | Concentration in uM |
| --- | --- |
| $CaCl_3$ (anhydrous) | 1800 |
| $FE(N_3O)_3 9H_2O$ | 0.2 |
| KCl | 5360 |
| $MgCl_3$ (anhydrous) | 812 |
| NaCl | 76000 |
| $NaHCO_3$ | 880 |
| $NaH_2PO_4 H_2O$ | 900 |
| $ZnSO_4 7H_2O$ | 0.67 |
| D-glucose | 25000 |
| phenol red | 23 |
| MOPS | 10000 |
| sodium pyruvate | 230 |
| L-alanine | 20 |
| L-arginine HCl | 400 |
| L-asparagine $H_2O$ | 5 |
| L-cysteine | 10 |
| L-glutamine | 500 |
| Glycine | 400 |
| L-histidine HCl $H_2O$ | 200 |
| L-isoleucine | 800 |
| L-leucine | 800 |
| L-lysine HCl | 5 |
| L-methionine | 200 |
| L-phenylalanine | 400 |
| L-proline | 67 |
| L-serine | 400 |
| L-threonine | 800 |
| L-tryptophan | 80 |
| L-tyrosine | 400 |
| L-valine | 800 |
| D-Ca pantothenate | 8 |
| choline chloride | 80 |
| folic acid | 8 |
| i-inositol | 40 |
| niacinamide | 30 |
| pyridoxal HCl | 20 |
| riboflavin | 1 |
| thiamine HCl | 10 |
| vitamin B12 | 0.2. |

12. The culture system of claim 9, further comprising one or more element selected from the group consisting of a member of FGF family, an extracellular matrix (ECM) component, an antibacterial agent, a non-essential amino acid, a neurotrophin, nicotinamide (NA), a bone morphogenic protein (BMP) antagonist and a serum free medium supplement.

13. The culture system of claim 12, wherein the FGF member is FGF-2, the ECM is selected from the group consisting of fibronectin, laminin and gelatin; the antibacterial agent is selected from the group consisting of penicillin and streptomycin; the TGFβ superfamily factor is activin A; the BMP antagonist is selected from the group consisting of noggin, chordin and gremlin; the neurotrophin is selected from the group consisting of BDNF, NT3, and NT4; and the serum free medium supplement is Nutridoma-CS.

14. The culture system of claim 9, wherein the human pluripotent SCs are pluripotent, human embryonic SCs (hESCs).

15. The culture system of claim 9, being free of laminin.

16. The culture system of claim 9, wherein the human pluripotent SCs are cultured in a bioreactor.

17. The method of claim 1, wherein the TGFβ superfamily factor is activin A.

18. The method of claim 1, wherein the culture system further comprises a member of the FGF family.

19. The method of claim 18, wherein the member of the FGF family factor is FGF-2.

20. A culture system comprising a suspension of human pluripotent stem cells (SCs) within in a culture medium comprising a basic medium, knockout serum replacement (KOSR), a TGFβ superfamily member, and one or more element selected from the group consisting of a member of the FGF family, an extracellular matrix (ECM) component, an antibacterial agent, a non-essential amino acid, a neurotrophin, nicotinamide (NA), a bone morphogenic protein (BMP) antagonist and a serum free medium supplement.

* * * * *